United States Patent
Chernyak

(10) Patent No.: US 9,668,649 B2
(45) Date of Patent: Jun. 6, 2017

(54) SYSTEM AND METHODS FOR MITIGATING CHANGES IN PUPIL SIZE DURING LASER REFRACTIVE SURGERY TO MAINTAIN ABLATION CENTRATION

(75) Inventor: Dimitri Chernyak, Sunnyvale, CA (US)

(73) Assignee: AMO Development, LLC, Santa Ana, CA (US)

(*) Notice: Subject to any disclaimer, the term of this patent is extended or adjusted under 35 U.S.C. 154(b) by 469 days.

(21) Appl. No.: 13/236,937

(22) Filed: Sep. 20, 2011

(65) Prior Publication Data

US 2012/0242956 A1 Sep. 27, 2012

Related U.S. Application Data

(60) Provisional application No. 61/384,411, filed on Sep. 20, 2010.

(51) Int. Cl.
| | | |
|---|---|---|
| *A61B 3/14* | (2006.01) | |
| *A61B 3/11* | (2006.01) | |
| *A61B 5/00* | (2006.01) | |
| *A61F 9/008* | (2006.01) | |

(52) U.S. Cl.
CPC ............ *A61B 3/112* (2013.01); *A61B 5/0077* (2013.01); *A61F 9/00804* (2013.01); *A61F 2009/00846* (2013.01)

(58) Field of Classification Search
CPC  A61B 3/14; A61B 3/113; A61B 3/152; A61B 3/0008; A61B 3/112; A61B 5/0077; A61F 2009/00872; A61F 9/00808; A61F 2009/00844; A61F 2009/00895; A61F 2009/00853; A61F 9/00; A61F 9/008;

(Continued)

(56) References Cited

U.S. PATENT DOCUMENTS

| | | | |
|---|---|---|---|
| 4,478,499 | A | 10/1984 | Hoerenz |
| 4,641,349 | A | 2/1987 | Flom et al. |
| 4,665,913 | A | 5/1987 | L'Esperance, Jr. |

(Continued)

FOREIGN PATENT DOCUMENTS

| | | |
|---|---|---|
| WO | 99/27334 A1 | 6/1999 |
| WO | 2006/032920 A2 | 3/2006 |

OTHER PUBLICATIONS

Bara, S. et al., "Positioning Tolerances for Phase Plates Compensating Aberrations of the Human Eye," Applied Optics, vol. 39, No. 19, pp. 3413-3420, Jul. 1, 2000.

(Continued)

*Primary Examiner* — Huy K Mai
*Assistant Examiner* — Daniele Manikeu
(74) *Attorney, Agent, or Firm* — Abbott Medical Optics Inc.

(57) ABSTRACT

Devices, systems, and methods perform diagnostic and/or treatment procedures on an eye using a pupilometer to determine a change in pupil size, a processor and a variable illumination source. In response to a change in pupil size as determined by the pupilometer, the processor may determine an optical light output sufficient to induce a pupillary response and mitigate the change in pupil size. The system directs the desired optical light output to the eye with the variable illumination source optionally to prevent the pupil size from exceeding certain limits so as to improve torsional tracking of markers of the eye.

46 Claims, 17 Drawing Sheets

(58) Field of Classification Search
CPC ........ A61F 2009/00846; A61F 9/00804; A61F 2009/0088
USPC ....... 351/200, 246, 210, 212, 204–209, 221, 351/159.78
See application file for complete search history.

(56) References Cited

U.S. PATENT DOCUMENTS

| | | | |
|---|---|---|---|
| 4,669,466 A | 6/1987 | L'Esperance | |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,163,934 A | 11/1992 | Munnerlyn | |
| 5,207,668 A | 5/1993 | L'Esperance, Jr. | |
| 5,214,455 A | 5/1993 | Penney et al. | |
| 5,219,343 A | 6/1993 | L'Esperance, Jr. | |
| 5,258,787 A | 11/1993 | Ito et al. | |
| 5,549,597 A | 8/1996 | Shimmick et al. | |
| 5,557,352 A | 9/1996 | Nordquist | |
| 5,617,872 A * | 4/1997 | Scinto et al. | 600/558 |
| 5,646,791 A | 7/1997 | Glockler | |
| 5,713,892 A | 2/1998 | Shimmick | |
| 5,740,803 A | 4/1998 | Gray et al. | |
| 6,004,313 A | 12/1999 | Shimmick et al. | |
| 6,095,651 A | 8/2000 | Williams et al. | |
| 6,271,915 B1 | 8/2001 | Frey et al. | |
| 6,315,413 B1 | 11/2001 | Shimmick et al. | |
| 6,322,216 B1 | 11/2001 | Yee et al. | |
| 7,044,602 B2 | 5/2006 | Chernyak | |
| 7,146,983 B1 | 12/2006 | Hohla et al. | |
| 7,431,455 B2 | 10/2008 | Chernyak | |
| 7,708,405 B2 | 5/2010 | Chernyak | |
| 7,744,216 B1 * | 6/2010 | Uhlhorn | 351/204 |
| 8,025,400 B2 | 9/2011 | Chernyak | |
| 2004/0252277 A1 * | 12/2004 | Chmielewski et al. | 351/209 |
| 2005/0254006 A1 * | 11/2005 | Dai | A61B 3/0025 351/159.73 |
| 2006/0077344 A1 | 4/2006 | Kashiwagi et al. | |
| 2006/0264916 A1 * | 11/2006 | Yee | A61F 9/008 606/5 |
| 2008/0009840 A1 * | 1/2008 | Chernyak | 606/5 |
| 2008/0212026 A1 * | 9/2008 | Molnar et al. | 351/206 |
| 2008/0273173 A1 * | 11/2008 | Grotehusmann et al. | 351/206 |
| 2009/0079940 A1 * | 3/2009 | Dai | A61B 3/0025 351/246 |
| 2009/0189998 A1 | 7/2009 | Nanu et al. | |

OTHER PUBLICATIONS

Chernyak, D. A., "Cyclotorsional Eye Motion Occurring between Wavefront Measurement and Refractive Surgery", Journal of Cataract Refractive Surgery, Mar. 2004, vol. 30, Issue 3, 633-8.

Chernyak, D. A., "Iris-based Cyclotorsional Image Alignment Method for Wavefront Registration", IEEE Transactions on Biomedical Engineering, Dec. 2005, vol. 52, Issue 12, 2032-40.

Wilson, M. A. et al., "The Julius F. Neumueller Award in Optics, 1989: Change of Pupil Centration with Change of Illumination and Pupil Size", Optometry and Vision Science, 1992, vol. 69, No. 2, 129-136.

Yang, Y. et al., "Pupil Location Under Mesopic, Photopic, and Pharmacologically Dilated Conditions", Investigative Ophthalmology & Visual Science, Jul. 2002, vol. 43, No. 7, pp. 2508-2512.

International Search Report of Application No. PCT/US2011/052343, mailed on Jan. 23, 2012. 3 pages.

* cited by examiner

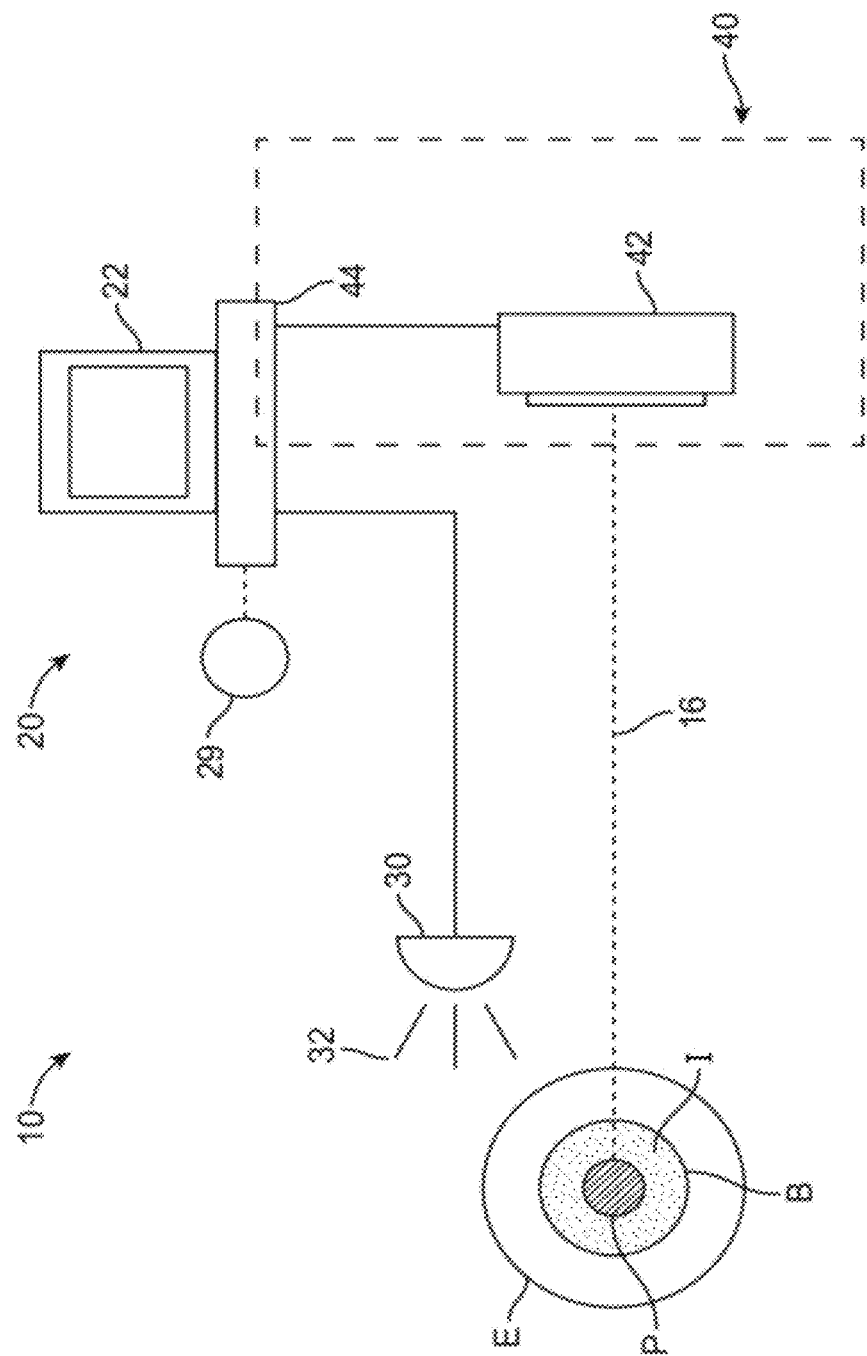

SYSTEM AND METHODS FOR MITIGATING CHANGES IN PUPIL SIZE DURING LASER REFRACTIVE SURGERY TO MAINTAIN ABLATION CENTRATION

CROSS-REFERENCES TO RELATED APPLICATIONS

The present application is a non-provisional of, and claims the benefit of U.S. Provisional Patent Application No. 61/384,411, filed Sep. 20, 2010, the entire contents of which are incorporated herein by reference.

The present application is generally related to the following commonly-owned applications: U.S. Ser. No. 12/197,774 filed Aug. 25, 2008 (U.S. Pat. No. 7,708,405); U.S. Ser. No. 11/088,010 filed Mar. 22, 2005 (U.S. Pat. No. 7,431,455); U.S. Ser. No. 12/731,959 filed Mar. 25, 2010; U.S. Ser. No. 09/545,240 filed Apr. 7, 2000 (U.S. Pat. No. 6,322,216); and U.S. Ser. No. 10/300,714 filed Nov. 19, 2002 (U.S. Pat. No. 7,044,602); the disclosures of which are incorporated herein by reference in their entireties.

BACKGROUND OF THE INVENTION

1. Field of the Invention

The present invention is generally related to systems and methods for diagnosis and/or treating vision in a patient. Embodiments of the invention encompass treatment techniques and systems that mitigate changes of the eye during a diagnostic and/or treatment procedure of the eye, in particular that mitigate changes in pupil size so as to allow for more accurate alignment and tracking of eye movements during a procedure. The present invention is particularly useful for enhancing the accuracy and efficacy of laser eye surgical procedures such as photorefractive keratectomy (PRK), phototherapeutic keratectomy (PTK), laser in situ keratomileusis (LASIK), and the like.

Laser eye surgical procedures benefit from precise alignment between the corneal tissues of the eye and a therapeutic laser beam. Known laser eye procedures generally employ an ultraviolet or infrared laser to remove a microscopic layer of stromal tissue from the cornea of the eye to change the cornea's contour for varying purposes, such as correcting myopia, hyperopia, astigmatism, and the like. Typically, the laser removes a selected portion of the corneal tissue to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser eye surgical systems often rely on a diagnostic refractive map of the patient's cornea to determine the precise contours to ablate with the therapeutic laser. For instance, wavefront technology measures and maps ocular aberrations of the eye, typically when the pupil is relatively large. The map is then used to create an ablation pattern which includes the positions as well as the depths of the proposed corneal ablations for correcting the aberrations. Precise alignment of the corneal tissues and the therapeutic laser beam is highly beneficial for the procedure. To ensure proper alignment between the ablation pattern and the surface of the cornea, systems rely on a variety of systems and methods, including the use of moveable apertures, controlled scanning systems, eye movement tracking mechanisms, and the like. These systems are generally adapted for use while the patient is awake. To adjust for movement of the eye during a procedure, tracking systems identify and track a reference feature of the eye, which may include any a pupil, an iris feature, a boundary of the iris and the sclera, and/or the location of the pupil center. The patient can further enhance alignment between the eye and the therapeutic laser beam by focusing on a fixation target during the procedure.

While laser scanning and eye tracking technology has provided significant benefits to refractive therapies in recent years, still further improvements would be desirable. For example, along with tracking overall changes in locations of the patient's eyes (such as when a patient slightly looks away from a fixation target), more recently developed systems have sought to both register a treatment with the eye and track an orientation of the eye during laser eye surgery (particularly the torsional orientation of the eye about the optical viewing axis). While both torsional registration and tracking have been performed, development and implementation of a highly robust torsional tracking system has been found to be particularly challenging. Work in connection with the present invention has identified changes in the eye during a procedure which may play a significant role in degradation and/or loss of tracking during a procedure. Hence, improved devices, systems, and/or methods which alleviate or overcome these challenges would be beneficial.

2. Description of the Background Art

U.S. Pat. No. 4,478,449, describes an operation microscope which incorporates an eye fixation device. U.S. Pat. No. 5,549,597, describes an in situ axis alignment module for determining the astigmatic axis of a patient, and for aligning the cylindrical axis of a laser ablation system for ophthalmological surgery. U.S. Pat. No. 5,258,787, describes an ophthalmologic apparatus having an illumination optical system for directing light onto a prescribed point of an eye, and an observation optical system for observing an image of the prescribed point. U.S. Pat. No. 5,557,352, describes a method and apparatus for measuring the visual acuity and refraction of the human eye during and immediately after ocular surgery.

U.S. patent application Ser. No. 09/545,240, entitled "Two Camera Off-Axis Eye Tracker for Laser Eye Surgery" as filed on Apr. 7, 2000, now issued as U.S. Pat. No. 6,322,216, describes an off-axis eye tracker which might be modified to measure pupil center drift. U.S. patent application Ser. No. 10/300,714, entitled "Methods and Systems for Tracking a Torsional Orientation and Position of an Eye" as filed on Nov. 19, 2002, now issued as U.S. Pat. No. 7,044,602, describes a torsional tracking system which uses image registering to track a position and a torsional orientation of the patient's eye during laser eye surgery so as to align a customized ablation profile with the patient's eye.

In light of the above, it would be desirable to provide improved ophthalmological systems, devices, and methods. It would be particularly desirable to provide methods and devices which can accurately register the patient's eye and mitigate changes in the eye characteristics to allow for tracking of positional movement and torsional rotation of the patient's eye. These methods and devices would be particularly useful for use with a customized ablation pattern. Additionally, it would be desirable to mitigate changes in pupil size to allow for more accurate tracking of positional movement and torsional rotation of the patient's eyes during other diagnostic and/or treatment procedures.

BRIEF SUMMARY OF THE INVENTION

The present invention provides methods and systems which can improve eye tracking and alignment during a diagnostic and/or treatment procedures of the eye, particularly laser eye surgery. Unlike systems which implicitly assume that pupil sizes do not change by clinically significant amounts during a refractive surgery procedure, exemplary embodiments of the present invention anticipate and mitigate significant changes to the pupil during a procedure. It is often assumed that if light levels remain fairly constant, the pupil size will not significantly change. However, pupil size may be affected by other factors, which include: stress, inability of the patient to focus on a target during a procedure, a change in optical distance of the viewing target, and an increase in cognitive load experienced by the patient during the procedure. An increase in cognitive load may result from accessing memory, increasing attention or concentration, sensory discrimination, or extreme emotional situations. For instance, fear experienced by a patient undergoing surgery may result in increased cognitive load causing the pupils to dilate. The pupils can also dilate in response to pain or contact of a sensory nerve, both of which may be experienced (to at least some extent) by a patient during a laser eye surgical procedure. These changes in pupil size will also often affect other characteristics of the pupil and the eye, such as pupil center location and iris texture. By anticipating and/or mitigating the dilations and contractions of the pupil (and associated pupil center shifts relative to static ocular landmarks of up to 0.5 mm or more depending on the change in the pupil diameter), the related negative impacts on tracking systems (particularly systems that track cyclorotational movement of the eye by registering a pupil center location or iris features relative to the cornea) can be decreased and/or avoided altogether. Similarly, tracking mechanisms that rely on the pupil position to steer the laser beam during laser refractive surgery and for which the pupil center position shifts relative to the cornea during the surgery, inhibiting changes in the size of the pupil may help avoid the targeted ablation center shifting as well as the resulting suboptimal results. Torsional eye trackers that rely on iris features to track the cornea during a procedure may benefit by anticipating and/or inhibiting dilations and contractions of the pupil during a laser eye surgical treatment, which cause changes to the iris which would otherwise make it more difficult to track the cornea and potentially lead to sub-optimal results.

In one aspect, the methods and system of the present invention may determine a change in pupil size, determine a desired optical light output in response to the change in pupil size sufficient to induce a desired pupillary response to mitigate the change in pupil size, and direct the desired optical light output to the eye. By mitigating changes in pupil size, embodiments of the present invention thereby reduce pupil drift to allow for more accurate tracking of positional movement and torsional rotations of the patient's eye during a diagnostic and/or treatment procedure.

In an exemplary embodiment, the method of the present invention comprises obtaining a first image of the eye with an imaging device, obtaining a second image of the eye, determining a change in pupil size between the first and second image, determining a desired optical light output in response to the change in pupil size so as to induce a desired pupillary response mitigating the change in pupil size, and directing the desired optical light output from a variable illumination source to the eye. In another aspect of the invention, the method may include centering and aligning a laser treatment with the first image of the eye and performing the laser treatment on the eye. The laser treatment may further include tracking positional movement and torsional rotation of the patient's eyes during a laser surgery procedure between first and second images.

In some embodiments, the change in pupil size comprises a change exceeding a certain pre-defined tolerance of a target pupil size. For instance, the tolerance may be +/−10% of the target pupil size. In another embodiment, determining the desired optical light output may include determining an optical light output within a pre-determined range of optical light outputs or an output within a certain tolerance of a reference output. For instance, the optical light outputs may be maintained within 25% of a reference optical output to ensure sufficient light for performing the procedure.

In an embodiment, the method determines a desired optical output sufficient to induce a desired pupillary response such that the desired pupillary response corresponds roughly to the calculated change in pupil size. The change in pupil size may be calculated from optical information obtained by an optical sensor. The optical information may comprise a plurality of images obtained by an imaging device or other optical information.

In another embodiment of the invention, the method comprises determining a relationship or trend of pupil size change for a given procedure, determining a desired optical light output as a function of the relationship or trend so as to induce a desired pupillary response to mitigate a change in pupil size as determined by the function, and directing the desired optical light output to the eye from a variable illumination source.

In another embodiment, the invention provides a system comprising a pupilometer generating pupil size signals, an illumination source having a variable optical light output, and a processor coupling the pupilometer to the illumination source. The processor is configured to transmit optical light output command signals to the variable source in response to the received pupil size signals so as to mitigate changes in pupil size so as to substantially maintain pupil size during a diagnosis and/or treatment of the eye. The pupilometer includes an optical sensor and a processor, which may be incorporated into the system processor. The optical sensor comprises a camera or other such imaging device.

In some embodiments of the invention, the pupilometer of the system comprises an imaging device configured to obtain a plurality of images of the eye from which the pupilometer can determine changes in pupil size. The pupilometer is coupled to the processor such that the processor can receive pupil size signals from the pupilometer. The processor is configured to determine a desired optical light output sufficient to mitigate the changes in pupil size as determined from the received pupil size signals. The processor is further coupled to the illumination source, which is configured to receive control signals from the processor that direct the source to direct the desired optical light output to the eye.

In another embodiment of the invention, the system comprises a variable illumination source coupled to a processor configured to direct a desired optical light output to the eye. The desired optical light output is a function of the pre-determined trend of pupil size change for a given procedure. The desired optical output is such that the anticipated pupillary response to the desired optical light output would mitigate the change in pupil size as determined from the pre-determined relationship. In one embodiment, the relationship may be a standard slope of the average pupillary response during the procedure or during a portion of the procedure. The desired optical output may be calculated from the trend or correlated from values derived from the trend.

In another aspect of the invention, the current system is incorporated into a laser eye surgical procedure having an eye tracking system. The tracking systems may comprise a torsional tracking systems that tracks cyclotorsional rotation. The tracking system may be configured to track a reference point of the eye, such as a pupil center location and an iris feature, by registering the reference point in images of the eye.

For a further understanding of the nature and advantages of the invention, reference should be made to the following description taken in conjunction with the accompanying drawings.

BRIEF DESCRIPTION OF THE DRAWINGS

FIG. 1 schematically illustrates an embodiment of the present invention;

DETAILED DESCRIPTION OF THE INVENTION

Figure 1A:
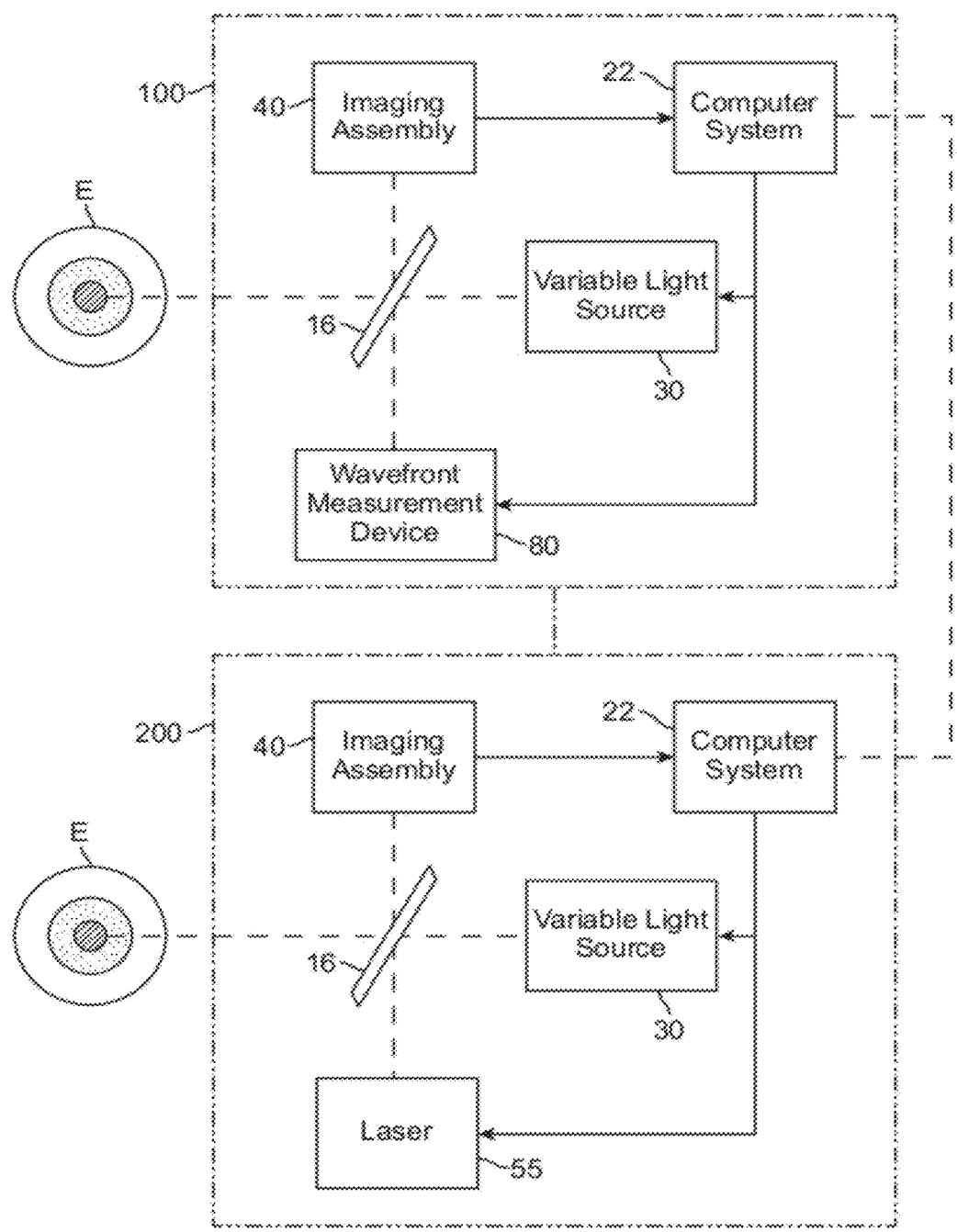
FIG. 1A schematically illustrates embodiments of the present invention as a diagnostic system and as a treatment system.

The present invention generally provides improved devices, systems, and methods for mitigating changes in pupil size during a diagnostic and/or treatment procedure of the eye, particularly during laser eye surgery procedures. In an exemplary embodiment, the invention provides a pupilometer capable of identifying changes in pupil size, an illumination source having a variable optical light output, and a processor. The pupilometer often calculates changes in pupil size, typically by comparing a time-sequence of images of the eye obtained by an image capture device. In response to the calculated change in pupil size, the processor determines a desired optical light output sufficient to induce a desired pupillary response so as to mitigate the calculated change in pupil size. The processor then sends command signals to the variable optical output which directs the desired optical light output to the eye so as to induce the desired pupillary response. Ideally, this process is performed in repeated iterations so as to mitigate changes in pupil size and allow for a diagnostic and/or treatment system to more accurately maintain alignment and track eye movements during a procedure. Preferably, the present system mitigates changes in pupil size such that particular aspects of the eye, such as pupil center location or iris features, do not change relative to the cornea so significantly as to impinge on locations and/or orientation tracking. For example, the process may be used after obtaining a pupil center shift from iris registration so that the pupil center shift obtained remains valid during the remainder of the procedure. By mitigating changes in pupil size, embodiments of the present system allow for tracking of eye movements using the pupil center location and/or iris features without requiring full registration between each tracking adjustment. Mitigating changes in pupil size is particularly useful as it increases the robustness of torsional tracking systems and aids in ensuring accurate alignment of an ablation pattern during a laser eye surgical procedure.

During a laser eye surgical procedure, the eye of a patient often gradually dilates during the procedure, even under substantially constant lighting conditions. Significant changes in pupil size not only cause the thickness and appearance of the iris I to change, but also causes the location of the pupil center to drift. This change in pupil center location is encompassed within the term "pupil center drift" as that term is used herein. It should be noted that this change in location of the pupil center is often separate from and in addition to any overall movement of the eye. Even if the eye were to remain at an overall fixed location in space so that the cornea and the retina of the eye did not move, as the pupil dilates from a first smaller pupil configuration to a larger pupil configuration, the center of the pupil undergoes a corresponding change in location. Since many laser eye surgery systems align to the pupil center, changes in location of the center of the pupil may cause misalignment of the ablation pattern. Additionally, torsional tracking systems typically align to markers on the eye, which may include the pupil center location and/or iris features. Loss of sufficient association between selected markers in iris and tracking images may result in loss of torsional tracking as the iris narrows, potentially leading to decentration of the ablation pattern and suboptimal treatment results. Examples of suboptimal results include astigmatism, halos, starbursts and decreased contrast sensitivity and decreased visual acuity in a patient's vision.

As the pupil changes from mesopic to photopic lighting conditions, the pupil center often drifts, as shown by the average pupil center shifts shown in Table 1 below. Generally as pupil size decreases, the pupil center will shift nasally. As pupil sizes increase, the pupil center shifts temporally. Significant changes in pupil size can occur quite rapidly and are often difficult to compensate for, especially when using a torsional tracking system. For example, if the pupil dilates significantly while its movement is being tracked with a torsional tracking system that detects eye movements based on pupil center location and/or iris features, the system may repeat a full registration to locate the shifted pupil center location or iris features of the dilated eye. Since full registration typically takes several seconds to complete, repeating full registration every time the pupil changes size is not desirable during a procedure. The claimed system, therefore, is advantageous as it mitigates the change in pupil size observed during surgery, thereby reducing pupil center drift allowing for improved torsional tracking and ablation centration. In particular, incorporating embodiments of the present invention into any number of laser eye systems improves the robustness of tracking algorithms, and in particular facilitates robust torsional tracking

TABLE 1

Pupil Center Drift from Mesopic to Photopic Lighting Conditions

| | Nasal shift (mm) | Superior Shift (mm) |
|---|---|---|
| VISX | 0.278 | 0.030 |
| Harvard | 0.054 | 0.004 |

The level at which changes in pupil size are mitigated can optionally be adjusted intermittently or continuously during a given diagnostic or treatment procedure. For instance, some procedures may be responsive to a threshold, relative to a target pupil size, so as to mitigate changes in pupil size when the pupil exceeds that threshold. For example, the threshold may range from about 1% to about 25% of the target pupil size. In a preferred embodiment, the threshold is about 10% of the target size or the original pupil size. The target size can be the pupil's original size at the beginning of the procedure or the target pupil size can be any given pupil size selected by the physician. In one embodiment of the invention, if the change in pupil diameter exceeds specified limits relative to the target pupil size, computer control software of the processor calculates an optical output sufficient to induce a desired pupillary response so as to mitigate the change in pupil diameter. The processor then sends a command signal to the variable optical output source, which in turn, directs the optical output to the eye to induce the mitigating pupillary response (e.g. increasing illumination when the pupil gets too large, or decreasing illumination when the pupil gets too small). By mitigating changes in pupil size, the system reduces changes in the position of the pupil center location and/or iris features relative to the cornea. For instance, if the system utilizes a torsional tracker which tracks changes in eye position and torsional displacement by tracking pupil center location and iris features, the tracker would not have to perform a second full registration of the tracking markers if the positions of the tracking markers (i.e. pupil center location, iris features) relative to the cornea do not substantially change.

Referring now to FIG. 1, system 10 includes a pupilometer 40, an illumination source 30 having a variable optical light output 32, and a processor 20. The variable illumination source 30 and pupilometer 40 are coupled to processor 20. Pupilometer 40 includes an optical sensor 42 and a processor 44 for determining changes in pupil size from optical information obtained by the optical sensor 42. The optical sensor 42 is coupled to the eye E by an optical path 16. Optical path 16 will often include additional optical imaging elements which are omitted from the simplified schematic of FIG. 1, including imaging lenses and the like, so as to image an iris I of eye E onto an image sensing surface of imaging device 42. Additional imaging components, such as apertures, filters, beam splitters, and the like can be used at least in part to define optical path 16, and the optical components will typically be held in place by an appropriate metallic or polymer support structure, which may be integrated into a housing extending from an eye cup adjacent to the eye E and/or beyond imaging device 42. Once the pupilometer 40 determines a change in pupil size, the pupilometer sends pupil size signals to processor 20. Processor 20 then determines a desired optical light output to induce a desired pupillary response to mitigate the change in pupil size. The processor 20 then sends command signals to illumination source 30 to direct the desired optical light output 32 to the eye, thereby inducing a pupillary response so as to mitigate the change in pupil size. Ideally, system 10 rapidly repeats this process, continually mitigating changes in pupil size to prevent significant changes in pupil size during the procedure.

Pupilometer 40 comprises or otherwise makes use of an optical sensor 42 coupled to a processor 44. The processor 44 of the pupilometer 40 can be included within processor 20 or can be a separate processor. Optical sensor 42 comprises an image capture device, a camera, or any optical sensor capable of detecting optical information sufficient for determining changes in pupil size. The change in pupil size can be derived from measurement of the entire pupil P or may include only a part of the pupil P and iris I or iris boundary B. Alternatively, the change in pupil size can be determined without directly measuring the size of the pupil P, for instance by registering multiple images of the pupil P or obtaining optical information from the pupil P and/or iris I as the pupil P changes in size. Typically, changes in pupil size are determined from comparing or registering multiple images of the eye E. However, optical information obtained from a sensor can be used to determine changes in pupil size without obtaining images, for instance optical changes at discrete points on the eye can indicate changes in the border of the pupil P. In an exemplary embodiment, the imaging device of the pupilometer 40 will obtain at least two images of the pupil, preferably a plurality of images in succession, so as to allow the pupilometer to calculate a change in the size of the pupil P relative to the first image or to a target pupil size. Changes in pupil size can also be expressed as a percentage by which the size of the pupil increases or decreases relative to the target pupil size.

In an exemplary embodiment, optical sensor 42 comprises a charge couple device ("CCD") which is sensitive to infrared light. Under infrared illumination, the pupil P of eye E will appear relatively dark as the infrared energy is not directly reflected by the clear corneal structure. The iris I surrounding the pupil P will present a much lighter shade to imaging device 42, with the white scleral tissue surrounding the iris presenting a still lighter shade. The relatively high contrast borders between the pupil and iris, and between the outer iris boundary and the surrounding tissues have a sufficiently high contrast image for determining pupil and iris size. Image processing software for use in determining the size and central location of pupil P and outer iris boundary B is commercially available from a number of sources. A variety of image processing software packages may be used, including (for example) INTEL IMAGE processing libraries or the like. Processors suitable for pupilometer 40 include PCs having at least the power of an INTEL Pentium® processor. Many of the processors could also be used, including those running the MacOS operating system from APPLE COMPUTERS, INC., a custom DSP device, or the like. Alternative embodiments may make use of software modified from that of a commercially available pupilometer, such as the P2000 line of pupilometers sold by PROCYON of the United Kingdom.

Optical sensor 42 may comprise a wide variety of alternative image capture structures, including complementary metal-oxide semiconductor ("CMOS") image capture devices, HRDC image capture devices, and the like. Optical sensor 42 may comprise, for example, a GW-902H model imaging device commercialized by GENWAC, INC. of New York and manufactured by WATEC CO., LTD. of Japan, which may take images using IR illumination with a wavelength of 880 nm. A variety of alternative imaging devices, imaging structures, or other sensors might also be used, including a GW-902B model imaging device from GENWAC; a Teli CE imaging device which may take images using IR illumination with a wavelength of 940 nm, and/or another imaging device selected from those commercialized as the CS8300B series by TOKYO ELECTRONIC INDUSTRY CO., LTD of Japan; a 4900 model series imaging device commercialized by COHU, INC., Electronics Division of San Diego; and the like. Optical path 16 will typically image a field of view of at least about 10.5 mm by 14.0 mm (measured at the plane of the iris of the eye), onto the image sensing surface, so as to image a sufficient portion of the iris with the imaging device.

Variable illumination source 30 comprises one or more light sources in optical communication with eye E. Illumination source 30 will typically have at least two settings of illumination levels, preferably having a plurality of illumination levels to create scotopic, mesopic, and photopic viewing conditions at the location of the eye E. The variable illumination source 30 can emit a constant optical light output or can emit a variable optical light output. An illumination source 30 may emit a variable optical light output by varying illumination from any or all of the sources or by altering the configuration, activating or deactivating light sources. An illumination source 30 comprising multiple light sources may include light sources having a constant illumination level, such as a light-emitting diode (LED). When system 10 is in use, illumination source 30 will illuminate the eye E with light having a wavelength suitable for inducing a pupillary response of the eye E. The optical light output from illumination source 30 may be directed to eye E by any manner sufficient to induce a pupillary response, including but not limited to ambient light, a halogen ring illuminator positioned around the eye, halogen oblique lights, a fixation light, an illuminated viewing target or any combination thereof.

In an exemplary embodiment, the intensity of the optical light output 32 from the variable illumination source 30 will be controlled by processor 20 using command signals sent to the illumination source 30. During operation of system 10, optical signals will typically be generated by optical sensor 42 and transmitted to processor 44 (which can be incorporated into processor 20). Processor 44 will determine a change in the size of the pupil P, if any. In response to a determination of pupil size change, processor 44 will generate pupil size signals. The pupil size signals need not necessarily communicate the size of the pupils, but may include signals containing optical information from which the change in pupil size can be determined. In response to the pupil size signals from processor 44, processor 20 determines a desired optical light output sufficient to induce a desired pupillary response to mitigate the change in pupil size. Processor 20 will then send a command signal to illumination source 30 to direct the desired optical light output 32 to eye E.

Processor 20 of system 10 will often comprise a computer 22, as illustrated in FIG. 1. In some embodiments, processor 20 will include a display 22 for showing an image of the structures of the eye, graphical representations of the size of the pupil, pupil drift or any other physiological characteristic measurements, and the like. Processor 20 will typically include a tangible media 29 embodying a machine readable code with programming instructions and/or data for implementing the method steps described herein. Tangible media 29 may comprise a magnetic recording media such as a floppy disk or magnetic tape, an optical recording media such as a CD or a DVD, an electronic media or memory such as a RAM or ROM, a non-volatile memory such as a USB memory stick device, or the like. In some embodiments, the machine readable code and/or data may be transmitted via an Internet, an intranet, a wireless transmission device, an optical network or cable, an electrical coaxial or twisted pair cable, or the like. Alternative processor structures might also be used, including specialized processor boards, distributed data software and/or hardware arrangements, and the like. When in the form of a personal computer, processor 20 will typically include user input devices such as a keyboard and/or mouse, input and output ports, software such as an operating system and a pupilometer user interface. In some embodiments, the physician may input data, which may include a target pupil size, upper and lower limits of a range of target pupil sizes, and upper and lower limits of a range of acceptable optical light outputs.

In an exemplary embodiment, system 10 operates to mitigate pupil size changes so as to maintain the pupil size within a pre-determined range of sizes or within a tolerance of a target pupil size. For instance, system 10 may operate to mitigate changes in pupil size that exceed ±10% of a target pupil size. The target size of the pupil may be the original size of the pupil, the size of the pupil during the mapping of ocular aberrations or a pupil size as defined by a physician. Ideally, system 10 performs the described processes in iterations performed in quick succession. As in a feedback mechanism, once a detected change in pupil size has been mitigated the system continues to detect and mitigate subsequent changes in pupil size relative to the target pupil size. The system 10 may mitigate changes in pupil size in discrete time periods. For instance, the system may mitigate pupil sizes once every second, multiple times per second, or the timing of the process may incorporate a lag to account for the pupillary response lag to changes in optical output. In some embodiments, the system 10 may use a time weighted average of pupil size changes to calculate a change in pupil size from which to determine the desired optical light output level. Alternatively, the system 10 may determine and mitigate pupil size changes dynamically as the pupillary response is induced.

In some embodiments, system 10 may determine the desired optical light output 32 based on a relationship or trend of pupil size change for a given procedure. The relationship may be based on optical data gathered during the procedure, an average of optical data from multiple patients, a predictive algorithm, or information gathered during characterization of a patient's pupillary response. For instance, the processor 20 may calculate a rate of pupil size change and incorporate this rate into the determination of a desired illumination level. The processor 20 may also utilize a database of average pupillary responses to determine the desired optical light output. In another aspect, the processor 20 may calculate a relationship between a patient's pupil size and photopic and scotopic light conditions, in effect characterizing an eye E of a patient to predict pupillary responses. Calculating such relationships is useful in determining desired light levels as pupillary responses may differ from patient to patient. For instance, an eye of a particular patient may be more sensitive to subtle changes in illumination than that of the average patient. By incorporating these relationships into the processor's determination of the desired optical light output, the processor 20 may increase the accuracy of the system 10 in mitigating changes in pupil size.

FIG. 1A schematically illustrates a simplified system of an embodiment of the present invention in a diagnostic system 100 and a treatment system 200, which may optionally be integrated into a diagnostic/treatment system. In this embodiment, the diagnostic system is a wavefront measurement system 100. The diagnostic procedure may be performed at the same time as the treatment procedure, or it may precede the treatment procedure by minutes, hours, days or weeks. The measurement system 100 is capable of generating images of the eye E and of providing information helpful for determining a desired corneal flap geometry. The flap geometry will often be referenced to the image, so that a relationship between the location of the flap incision and the image data can be established. The corneal flap geometry is often linked to a feature or reference location on the eye E which can be identified in the image, such as a pupil center (located at the center of the inner iris boundary), the center of the outer iris boundary or limbus, natural markings included in the iris, visible limbal landmarks or features, and the like. Along with locating and/or determining the desired corneal flap geometry, the measurement system 100 may also include at least a portion of a processor system capable of calculating a set of treatment instructions to be used by a laser incision system, such as femtosecond laser system 200.

The exemplary measurement system 100 includes a wavefront measurement device 80, such as a wavefront aberrometer, variable light source 30, computer system 22, and an imaging assembly 40. Imaging assembly 40 captures an image of the eye at substantially the same time (so that the eye does not move between the image and the measurement) that the wavefront measurement device 80 directs a beam toward the eye of a patient in a diagnostic procedure under the direction of computer system 22. Measurement device 80 and imaging assembly 40 may be optically coupled to optics 16, which directs a measurement beam to the eye E, an image from the eye to the imaging assembly 40, and a measurement image from the eye back to the measurement device. Variable light source 30 may be optical coupled to optics 16 or may be optically coupled to the eye E directly or through another path independent of optics 16. The computer system 22 optionally determines a desired corneal flap geometry based on the images generated by the imaging assembly 40, often with the input of a system operator. The computer may store the corneal flap geometry, wavefront measurements and images of the patient's eye. One or more different incisions, a set of incisions or the like may be calculated for a desired corneal flap geometry. While the incisions are generally applied to form the desired corneal flap geometry, an individual incision or set of incisions may optionally be calculated to be formed in the cornea in other embodiments. The computer system 22 also calculates a change in pupil size from the images obtained by imaging assembly 40. From the calculated change in pupil size, computer system 22 determines a desired optical output sufficient to mitigate the change in pupil size according to pre-defined limits or user-defined variable. Computer system 22 then sends a control signal to variable light source 30 which directs the desired optical light output to the eye E so as to induce a pupillary response to mitigate the calculated change in pupil size. As the wavefront measurement and image are substantially contemporaneous, and as the structures of the imaging assembly and the measurement device are optically and/or mechanically coupled, the location information included in the image and the measurement can be associated. Computer system 22 may use the images of the eye E to contemporaneously direct measurement by the wavefront measurement device 80 and induce pupillary responses to mitigate changes in pupil size by the variable light source 30 during the measurement procedure. In some embodiments, the computer processor 22 may also generate and save additional treatment information, such as an ablation profile or laser sculpting based on the image data that can later be downloaded into a refractive laser system 110 (see FIG. 1B). Suitable measurement systems may include structures based on the WaveScan Wavefront® System commercially available from Abbott Medical Optics, Inc. (AMO) of Santa Ana, Calif., the Zyoptix® diagnostic workstation commercially available from Bausch and Lomb of Rochester, N.Y., and others.

The laser system 200 includes a laser 55, such as a femtosecond laser, an imaging assembly 40 that obtains an image of the eye, a computer system 22 and a variable light source 30. Images from imaging assembly 40 are used by computer system 22 to align an ablation profile to the cornea and may be further used by computer system 22 to track positional and/or rotational movements of the eye by registering features of the eye E. The computer system 22 also calculates a change in pupil size from the images obtained by imaging assembly 40. From the calculated change in pupil size, computer system 22 determines a desired optical output sufficient to mitigate the change in pupil size according to pre-defined limits or user-defined variable. Computer system 22 then sends a control signal to variable light source 30 which directs the desired optical light output to the eye E so as to induce a pupillary response to mitigate the calculated change in pupil size. Images from imaging assembly 40 are substantially contemporaneous with the incision of the eye using laser 55 and with adjustment of the variable light source 30 by the computer system 22. The imaging assembly 40 and laser 55 are mechanically and/or optically coupled together, so that the images from imaging assembly 60 can be used by computer system 22 to help direct a laser beam 55 to the eye E of the patient during a treatment procedure. Treatment of the eye E with laser 55, the computer system 22 adjusts variable light source 30 to induce a pupillary response so as to mitigate changes in pupil size during the procedure, thereby reducing changes in the tracked features of the eye relative to the cornea. Laser 55 and imaging assembly 60 may be optically coupled to optics 75, which directs beam 65 to the eye E. Variable light source 30 is also coupled to eye E, either directly or indirectly, for instance through optics 16. Computer system 22 will generally direct pulses of laser energy toward the cornea to form an incision in the cornea so as to form a flap of corneal tissue exposing the stroma underlying the corneal epithelium. Subsequent ablation or removal of the exposed stroma can alter the refractive characteristics of the eye. In some embodiments, the ablation profile generated with the measurement system 100 will be downloaded into computer system 22, and the corneal correction may be performed using the femtosecond laser 55. Suitable femtosecond laser systems may include the iFS™ Advanced Femtosecond Laser system commercially available from AMO.

Embodiments of the present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy. Aspects of techniques described herein can be implemented in a variety of laser and aberrometer devices, including without limitation the VISX WaveScan WaveFront® System and VISX STAR 54® Excimer Laser System, the Wavelight® Alegretto and Tscherning-based aberrometer; the Alcon Ladarvision® lasers and Ladarwave® aberrometer; the Bausch and Lomb Zyoptix® laser and related aberrometer, and the Zeiss® laser and WASCA® aberrometer.

Figure 1B:
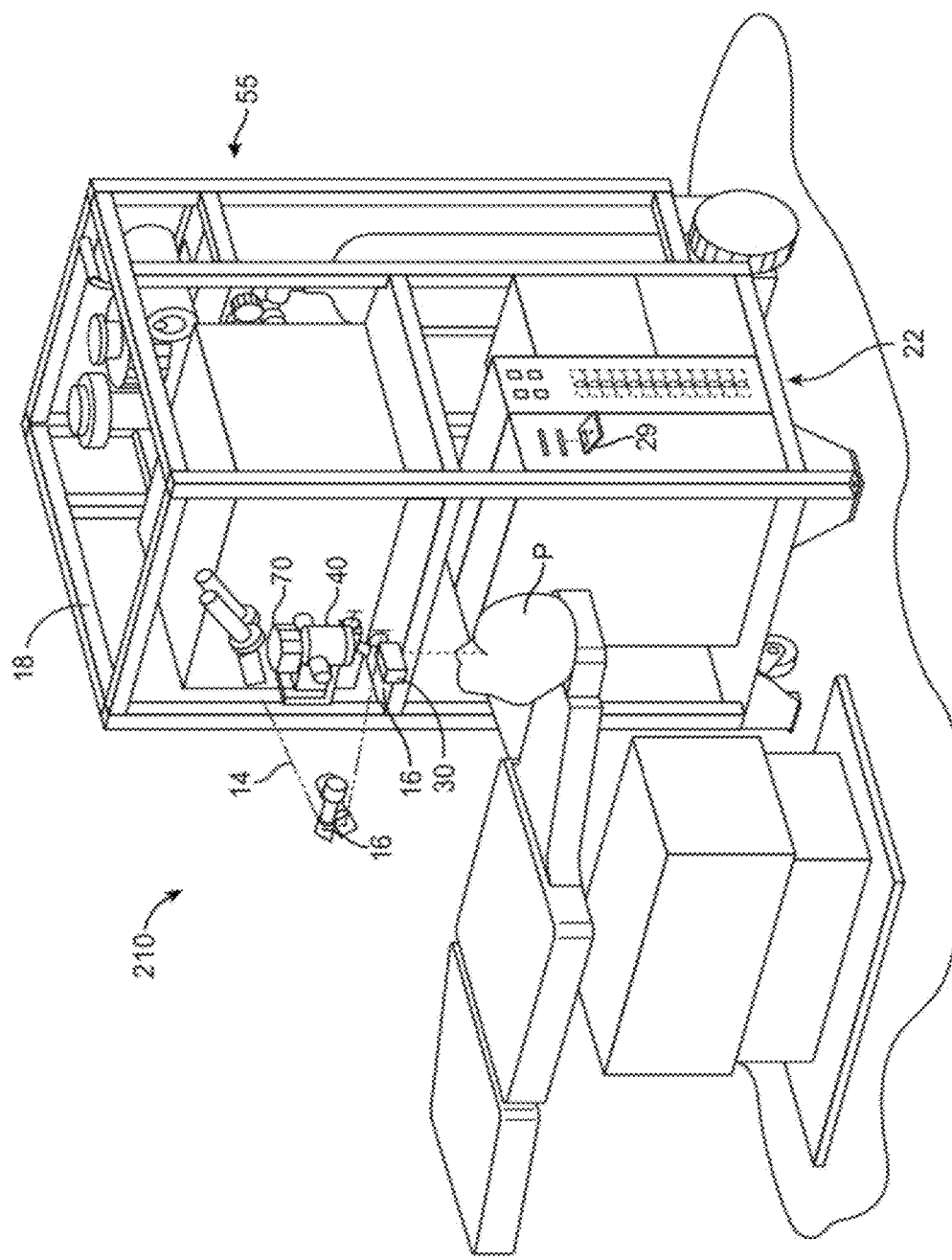
FIG. 1B illustrates a laser ablation system according to an embodiment of the present invention.

Turning now to the drawings, FIG. 1B illustrates a laser eye surgery system 210 of the present invention, including a laser 55 that produces a laser beam. Laser 55 is optically coupled to laser delivery optics 16, which directs laser beam to an eye E of patient P. A delivery optics support structure (not shown here for clarity) extends from a frame 18 supporting laser 55. A microscope 70 is mounted on the delivery optics support structure. A pupilometer 40 is positioned so as to measure the size of the pupil of the eye. Often the pupilometer 40 will be coupled to microscope 70 which will be used to image a cornea of eye E. Laser 55 generally comprises an excimer laser, ideally comprising an argon-fluorine laser producing pulses of laser light having a wavelength of approximately 193 nm. Laser 55 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in some embodiments of the present invention.

Laser system 210 will generally include a computer 22 or programmable processor 20 coupled to the pupilometer 40 or other imaging device, the laser 55 and the variable illumination source 30. Processor 20 may comprise (or interface with) a conventional PC system including the standard user interface devices such as a keyboard, a display monitor, and the like. Processor 20 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 20 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 20, the storage media may also be remotely operatively coupled with processor by means of network connections such as the internet, and by wireless methods such as infrared, Bluetooth, or the like.

Laser 55 and delivery optics 16 will generally direct laser beam to the eye of patient P under the direction of a computer 22 during which variable light source 30 emits light to the eye along optical path of delivery optics 16. Computer 22 will often selectively adjust laser beam contemporaneous with adjusting the output of the variable illumination source 40. The computer 22 adjusts the laser beam to expose portions of the cornea to the pulses of laser energy so as to effect a predetermined sculpting of the cornea and alter the refractive characteristics of the eye. Contemporaneous with the laser beam treatment, computer 22 selectively adjusts the variable light source 30 to direct an optical output to the eye sufficient to mitigate the calculated changes in pupil size (as calculated from images obtained from pupilometer 40). The computer 22 may also adjust the variable light source 30 to effect a pre-determined change in pupil size if desired. In many embodiments, the laser beam, the laser delivery optical system 16, and the variable light source 30 will be under computer control of processor 22 to effect the desired laser sculpting process, with the processor effecting (and optionally modifying) the pattern of laser pulses and the light output of the variable light source. The desired light outputs may by summarized in machine readable data of tangible storage media 29 in the form of a treatment table, and the treatment table may be adjusted according to feedback input into processor 22 from an automated image analysis system or pupilometer 40 in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Optical light source 30 may be adjusted to produce the desired pupillary response using a variety of alternative mechanisms. The light source 30 may be selectively limited using one or more variable apertures. An exemplary variable aperture system having a variable iris and a variable width slit is described in U.S. Pat. No. 5,713,892, the full disclosure of which is incorporated herein by reference. Typically, halogen ring illuminators and halogen oblique lights can be adjusted by discrete steps, such as in a dimmer switch. The fixation light source, where the patient is instructed to look during surgery, can also be made adjustable. In some embodiments, the source may include an existing illumination source in a diagnostic or treatment device, such as the visible light source in the iDesign diagnostic device. Other illumination sources, including those based on LEDS, which may be used as alternative or additional sources of visible illumination of the eye during surgery. Using a plurality of light sources, as described above, allows for high dynamic range of illumination and further allows for optimization of light control to correct pupil size and/or provide a well illuminated surgical area for the operating physician.

Additional components and subsystems may be included with laser system 210, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 1C:
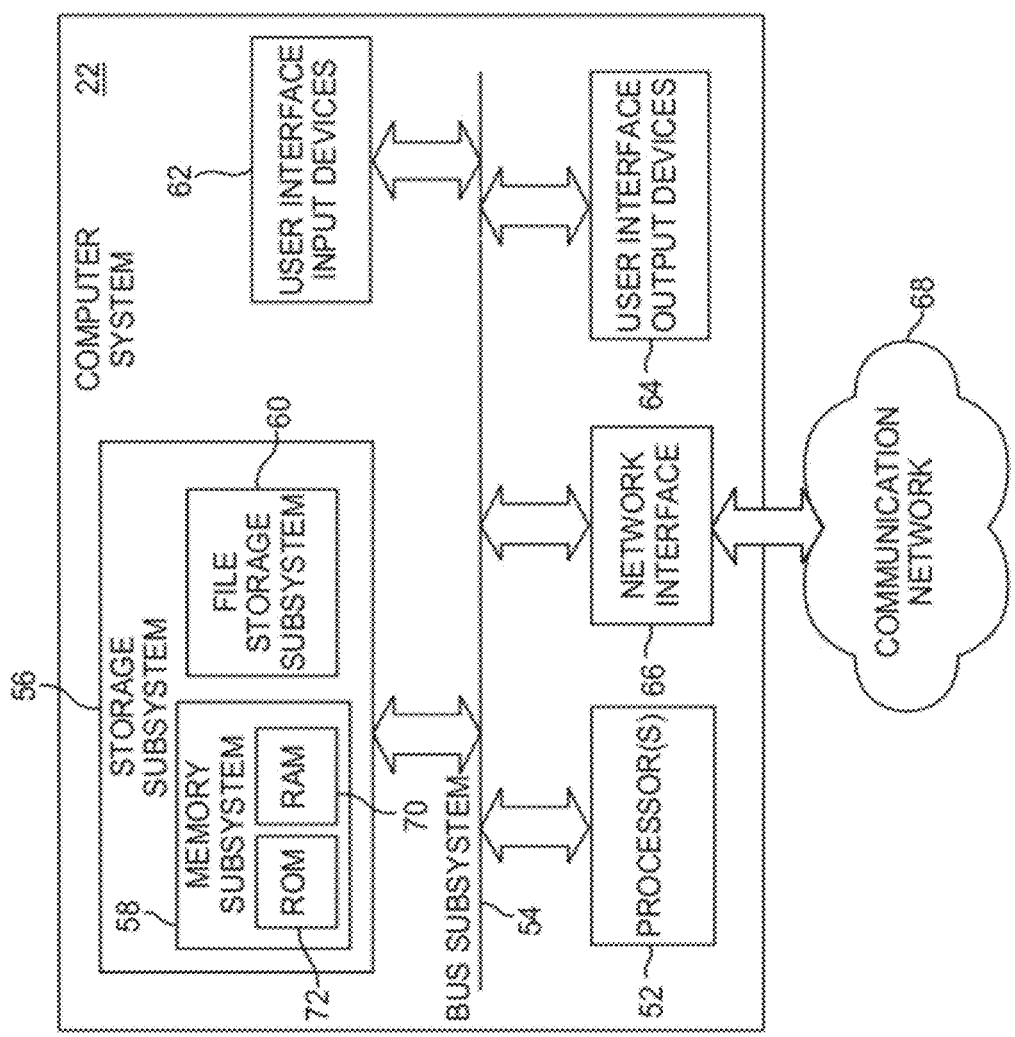
FIG. 1C illustrates a simplified computer system according to an embodiment of the present invention.

FIG. 1C is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as a wavefront measurement system.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of any of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1B) which may optionally embody pupil size data, anticipated pupillary response tables, wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of embodiments of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 1C is intended only as a specific example for purposes of illustrating one embodiment of the present invention. Many other configurations of computer system 22 are possible having more or less components than the computer system depicted in FIG. 1C.

Figure 1D:
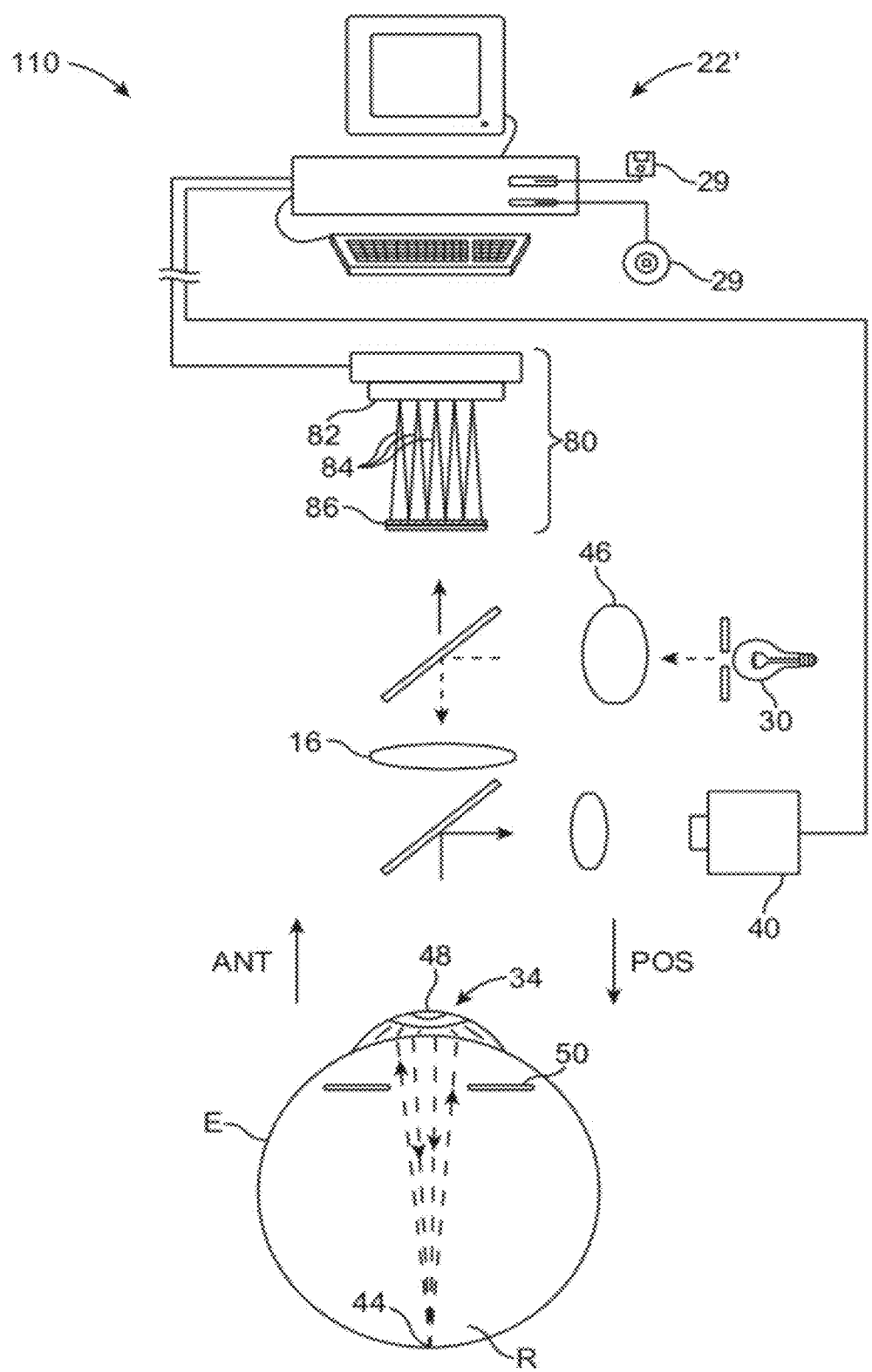
FIG. 1D illustrates a wavefront measurement system according to an embodiment of the present invention.

Referring now to FIG. 1D, one embodiment of a laser eye wavefront system 110 is schematically illustrated in simplified form. More specifically, system 110 includes a wavefront sensor 80, a variable light source 30, such as an LED, which can be adjusted to direct a desired light output to the optical tissues of eye E so as to induce a pupillary response. In very general terms, measurement system 110 is configured to perform wavefront measurements and detect changes in pupil size during a procedure and adjust the variable optical light source in response to a calculated change in pupil size to effect a desired mitigating pupillary response. System 110 may be used in conjunction with laser system 210. The wavefront sensor 80 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1B and 1C. Computer system 22' may be in communication with computer system 22 that directs laser surgery system 210, or some or all of the components of computer system 22, 22' of the wavefront measurement system 110 and laser surgery system 210 may be combined or separate. If desired, data from wavefront sensor 80 may be transmitted to a laser computer system 22 via tangible media 29, via an I/O port, via an networking connection 66 such as an intranet or the Internet, or the like.

Wavefront sensor 80 generally comprises a lenslet array 86 and an image sensor 82. As the image from retina R is transmitted through optical tissues 34 and imaged onto a surface of image sensor 82 and an image of the eye pupil P is similarly imaged onto a surface of lenslet array 886, the lenslet array separates the transmitted image into an array of beamlets 84, and (in combination with other optical components of the system) images the separated beamlets on the surface of sensor 82. Sensor 82 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Optical light source 30 or another projection source generally projects an image in a posterior orientation through optical tissues 34 onto retina R as indicated in FIG. 1D. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Eye E generally defines an anterior orientation ANT and a posterior orientation POS. An image is protected from optical light source 30 or another light source in optical communication with eye E. The image is projected in a posterior orientation through optical tissues 34 onto retina R as shown in FIG. 1D.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 80. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally beneficial to have a well-defined and accurately formed image 44 on retina R.

Optical light source 30 is a variable optical light source and is coupled with the process or computer 22' such that the processor can send command signals to the optical light source to direct a desired optical output level of illumination to the eye. The variable optical light source 30 may be the same optical source that projects an image on the retina or may be separate, such as a halogen ring placed near the eye E during the procedure. Computer 22' calculates changes in pupil size during the procedure from images obtained by the imagine assembly 40. In response to a calculated change in pupil size, computer 22' determines a desired optical output sufficient to induce a pupillary response, such that the pupillary response mitigates the change in pupil size. In response to the calculated change in pupil size, computer 22' sends a command to optical light source 30 to direct the desired optical output to the eye E to induce the mitigating pupillary response.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 40 (FIG. 1D) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While many methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from an imaging device 40. Imaging device 40 may also act as a pupilometer obtaining images of at least a portion of the pupil from which the computer 22' can calculate changes in pupil size. In the exemplary embodiment, imaging assembly 40 images pupil 50 so as to determine a position of the pupil for registration of the wavefront sensor data relative to the optical tissues, for instance by registering pupil center location and/or iris features relative to the cornea. By monitoring changes in pupil size and mitigating such changes through the variable optical output, the system reduces change in pupil center location and iris features relative to the cornea improving tracking and registration of the cornea during the procedure.

Figure 1E:
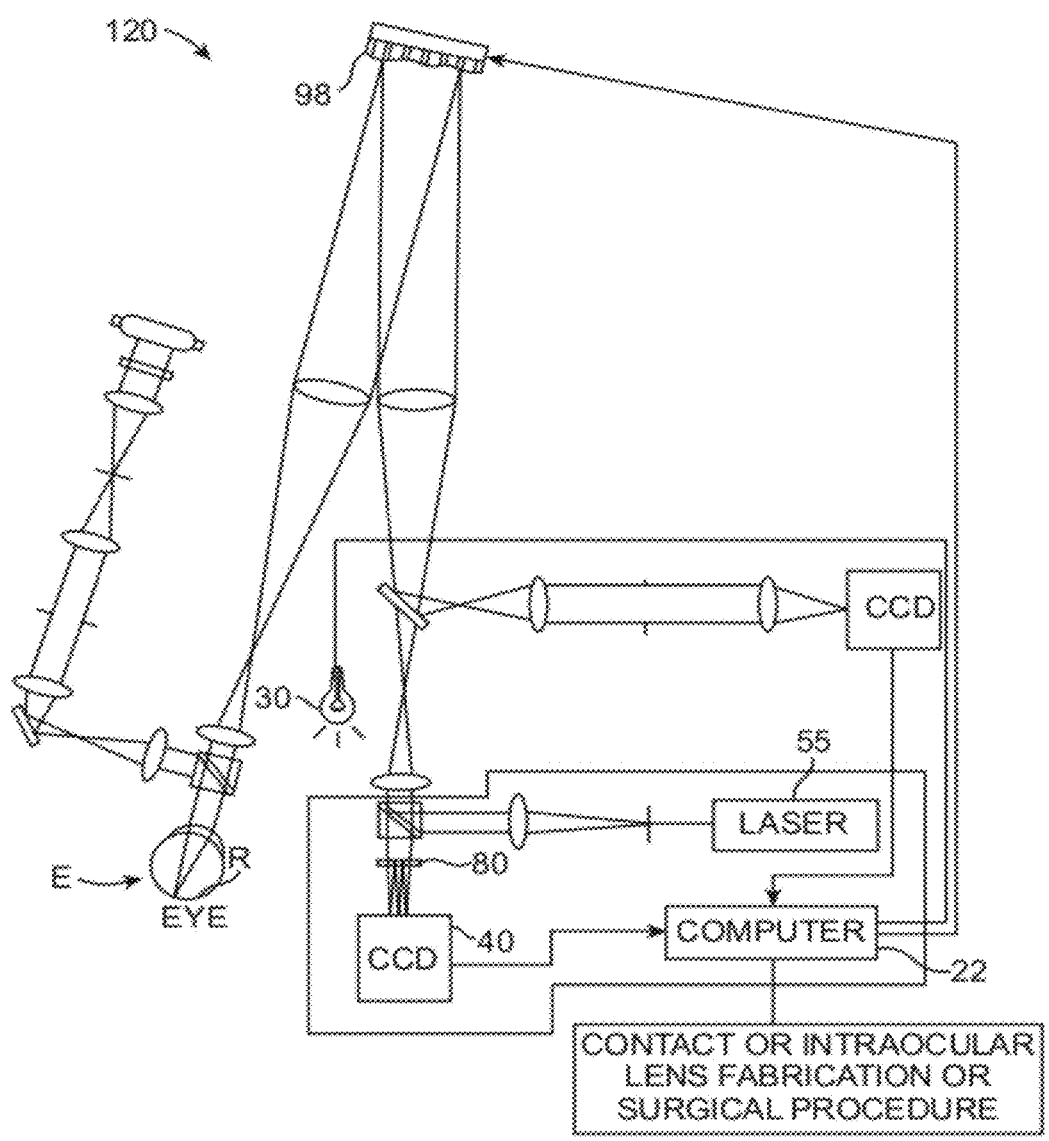
FIG. 1E illustrates another wavefront measurement system according to an embodiment of the present invention.
Figure 2:
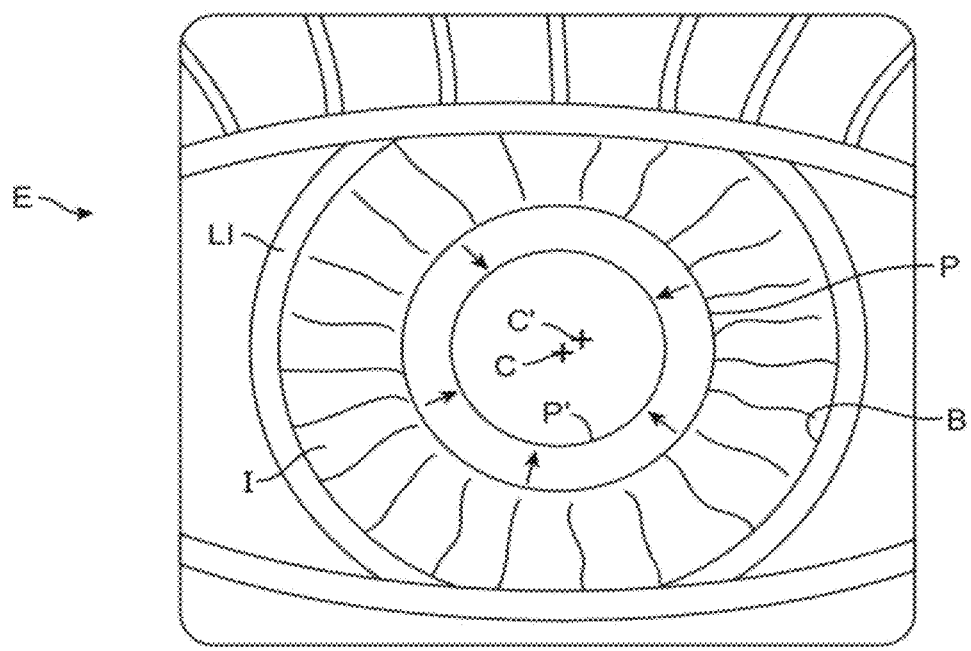
FIG. 2 illustrates an image captured by an image capture device of the system of FIG. 1 and also shows changes in pupil center location or pupil drift.

An alternative embodiment of a wavefront measurement system 120 is illustrated in FIG. 1E. The major components of the system of FIG. 1E are similar to those of FIG. 1D. Additionally, FIG. 1E includes an adaptive optical element in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The computer 22 calculates any changes in pupil size from images obtained from the CCD and determines the desired optical output and commands variable optical light source 30 to direct the desired optical output, according to the parameters of the system. The structure and use of the system of FIG. 1E are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No.

6,271,915, the full disclosure of which is incorporated herein by reference. It is appreciated that any wavefront aberrometer could be employed for use with embodiments of the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

Referring to FIGS. 2-4B, FIG. 2 generally shows an image of eye E as obtained by camera 40 taken as a pupil constricts (along with a superimposed contracted pupil P', pupil center locations C, C', and the like). P represents a dilated pupil, while P' represents a constricted pupil. Camera 40 will generally comprise an image capture device or other optical sensor capable of detecting optical information sufficient for measurement of the pupil center location, pupil size, outer iris boundary B size and/or location, the location of other additional or alternative reference structures on the eye, and the like. As illustrated in FIGS. 2-4B, a location of the iris I (and all other tissues of the eye E) will change with saccadic and other movements of the eye. Using the difference in relative contrast between the pupil P and surrounding iris I, pupilometer 40 determines a diameter of pupil P and identifies a center location PC1. Similarly, using the same image captured by camera 40, processor 20 also determines a diameter of the outer iris boundary B and a location of the boundary center BC1, generally by using the contrast differential between the outer iris boundary and the surrounding tissues. Based on the difference in location between the outer iris boundary center BC1 and the pupil center boundary PC1, processor 20 identifies a horizontal center difference $\Delta x$ and a vertical center difference $\Delta y$. FIG. 3A and FIG. 3B shows a plot of the identified $\Delta x1$ and $\Delta y1$ locations as the pupil size changes.

Figure 3A:
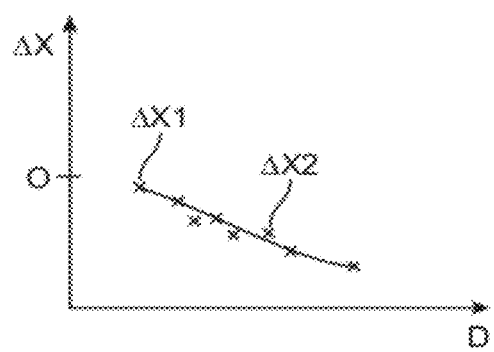
FIGS. 3A and 3B graphically illustrate a relationship between pupil center drift for the left eye and right eye of a patient as the pupil changes size, respectively.
Figure 3B:
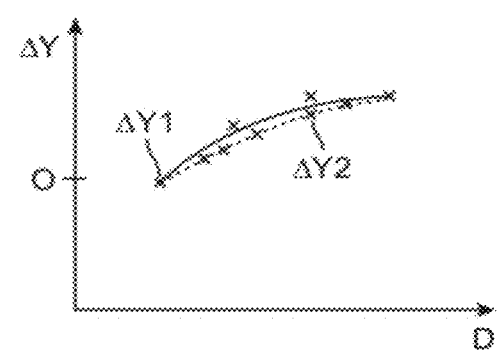

Referring now to FIGS. 2, 3A-3B and FIG. 4B, a subsequent image taken shows the constricted smaller pupil size P' after pupil constriction. Processor 20 once again determines a size and center location of the constricted pupil PC2 relative to the concurrent outer iris boundary center BC2 so as to determine new horizontal and vertical center offsets $\Delta x2$ and $\Delta y2$. By measuring a series of different viewing distances, horizontal and vertical pupil center drift with changing viewing distance D may be plotted as shown in FIG. 3A and FIG. 3B.

Image processing software for use in determining the size and central location of pupil P and outer iris boundary B is commercially available from a number of sources. A variety of image processing software packages may be used, including (for example) INTEL IMAGE processing libraries or the like. Processors suitable for pupilometer include PCs having at least the power of an INTEL Pentium® processor. Many of the processors could also be used, including those running the MacOS operating system from APPLE COMPUTERS, INC., a custom DSP device, or the like. Alternative embodiments may make use of software modified from that of a commercially available pupilometer, such as the P2000 line of pupilometers sold by PROCYON of the United Kingdom.

Figure 5:
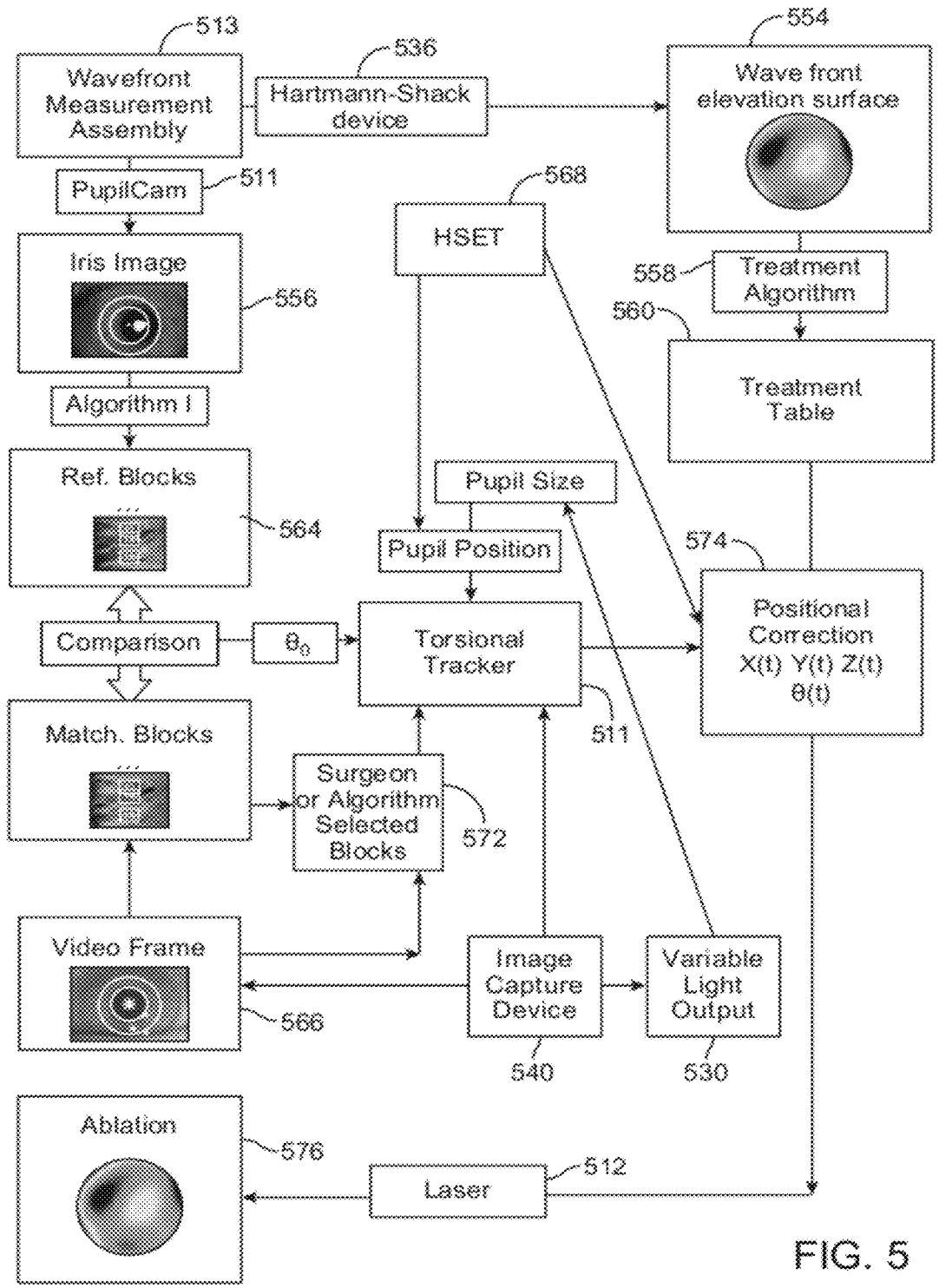
FIG. 5 illustrates an exemplary embodiment of the present invention.

Referring now to FIG. 5, schematically illustrates one embodiment of a method of the present invention as used in a laser eye system having torsional tracking and a wavefront assembly. Wavefront measurement assembly 513 can use wavefront sensors 536, such as Hartmann-Shack sensors, for obtaining a wavefront elevation surface 554 of the patient's eye. Wavefront elevation surface 554 can be run through a treatment algorithm 558 to generate a treatment table or ablation profile 560 that is customized to correspond to the patient's wavefront elevation surface 554. As noted above, ablation profile 560 can be calculated by a processor of wavefront device 510, laser system 515, or by a separate processor and stored in a memory of computer 22.

During the calculation of the wavefront elevation surface, imaging assembly 540 can concurrently obtain an image 556 of the patient's eye, e.g., pupil and iris. The image of the patient's eye 556 can be analyzed by an algorithm 562 that locates the center of the pupil and/or iris, calculates the radius of the pupil and/or iris, and locates markers 564 in the patient's iris for subsequent registration and tracking.

In order to register the ablation profile 560 and the patient's eye during the laser treatment, the ablation pattern and the patient's eye should share a common coordinate system. Thus, ablation profile 560 should be positionally and torsionally aligned with the patient's eye when the patient's eye is positioned in the path of the laser beam. Additionally, the translational and torsional orientation of the patient's eye should be tracked during the surgical procedure to ensure an accurate delivery of the ablation profile.

To torsionally align (i.e., register) the ablation profile 560 with the patient's eye E, the reference or iris image 556 of the eye needs to have a unique coordinate transformation to an image of the eye taken by the imaging device 540 of the laser system so as to determine the positional differences and torsional offset between the two images of the eye, $\theta_0$. In exemplary embodiments, image capture device 540 that can obtain streaming video of the patient's eye. One frame 566 of the streaming video, typically the first frame of the streaming video, can be analyzed by the computer processor to locate the pupil center, pupil size, iris center, and/or markers 564 that were originally located in the reference image 556. Once the pupil center, iris center, and/or markers 564 are located, a pupil size characteristic is calculated, as well as a torsional offset, $\theta_0$, between reference image 556 and video frame image 566 of the patient's eye.

Once the pupil size characteristic is determined, the computer can determine a change in pupil size and calculate a desired optical output to induce a desired pupillary response so as to mitigate the change in pupil size. Once the desired optical output is calculated, the computer sends a signal to the variable light output 530, which then directs the desired optical output to the patient's eye E so as to induce the desired pupillary response, thereby mitigating the change in pupil size. Mitigating the change in pupil size allows for the system to reduce changes in the position of the markers used in tracking relative to the cornea, in particular the pupil center location and iris features. This aspect of the invention allows for the torsional tracking system to track the markers and adjust for positional and torsional movement without requiring a subsequent full registration to determine if the pupil center location and/or iris features have moved relative to the cornea.

Once the torsional offset $\theta_0$ is determined, the computer can track the translational position (x(t), y(t), and z(t)) of the patient's eye E with a high speed eye tracker (HSET) 568 and the torsional orientation ($\theta(t)$) of the eye with a torsional tracker 570. Because the position of the center of the pupil is tracked with the HSET 568, the torsional tracker 570 generally estimates the position of the markers 564 with respect to the pupil center.

If the HSET 568 determines that the patient's eye has moved (relative to video frame image 566), the computer can correct the delivery of the customized ablation pattern by adjusting the patient's customized treatment table 560 by adding in the translation and torsional measurements into the table. The treatment table can be adjusted such that at time t, if the overall rotation angle of the eye is θ(t), and the next pulse of the laser is supposed to be delivered at location (x,y) on the cornea, the new location of the delivery of the pulse can be defined by:

$$\begin{pmatrix} x' \\ y' \end{pmatrix} = \begin{bmatrix} \cos\theta & -\sin\theta \\ \sin\theta & \cos\theta \end{bmatrix} \begin{pmatrix} x \\ y \end{pmatrix}$$

To track the torsional movement of the patient's eye, torsional tracker 570 can use the markers 564 identified above, other high-contrast iris patches, or if the patient's iris contains too little texture, the surgeon will have an option of drawing artificial landmarks 572 on the eye for tracking Optionally, in some embodiments it is possible for the algorithm to decide if artificial markers are required. Contemporaneous with the tracking of the markers, the system detects changes in pupil size and adjusts the optical output from the variable optical light source 530 to mitigate changes in pupil size allowing for more accurate torsional tracking.

The pupil size of the patient's eye can be monitored and analyzed by a computer processor in real-time so that the pupil size information can be used to adjust the desired optical output from the optical light source 530 so as to constrain the pupil size within +/−10% of the original pupil size. The pupil size of the eye can be tracked and analyzed concurrently with the translational position and the torsional orientation of the patient's eye with the torsional tracking system. Pupil size and positional data can be tracked concurrently in real-time or, alternatively, may be tracked at different rates. The translational position and torsional orientation of the patient's eye can be tracked and analyzed by a computer processor in real-time so that the x(t), y(t), z(t) and θ(t) information 574 can be used to adjust the customized treatment table 560 so that laser 512 delivers the appropriate ablation pattern 576 to the patient's eye. Various embodiments of this torsional tracking system are described in U.S. Pat. No. 7,044,602; the disclosure of which is incorporated herein by reference in their entirety.

Figure 6:
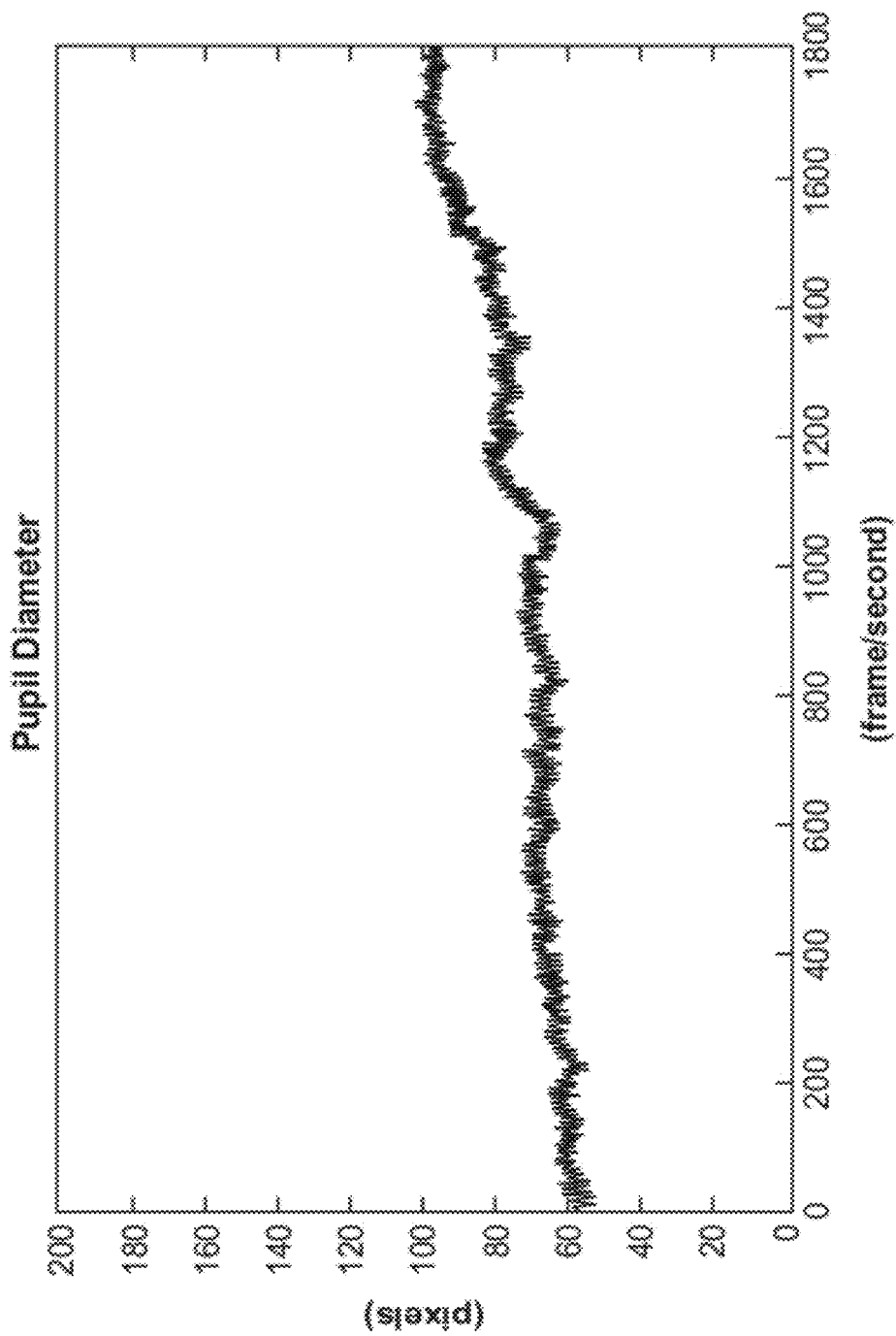
FIG. 6 illustrates change in pupil size over time as observed during a procedure.

FIG. 6 shows the increase in pupil size P observed during a laser eye procedure under substantially constant lighting conditions. As shown in FIG. 6, the pupil size P changes significantly, increasing from about 60 pixels in diameter at the beginning of the surgery to about 100 pixels by the end of the surgery, indicating a change in pupil size of about 67%.

Figure 4A:
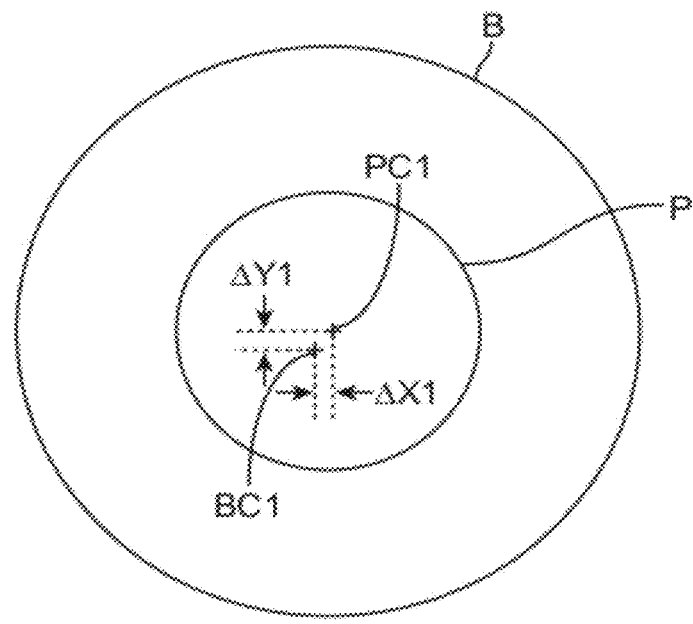
FIGS. 4A and 4B schematically illustrates pupil center drift from different images by identifying centers of a pupil and an outer iris boundary.
Figure 4B:
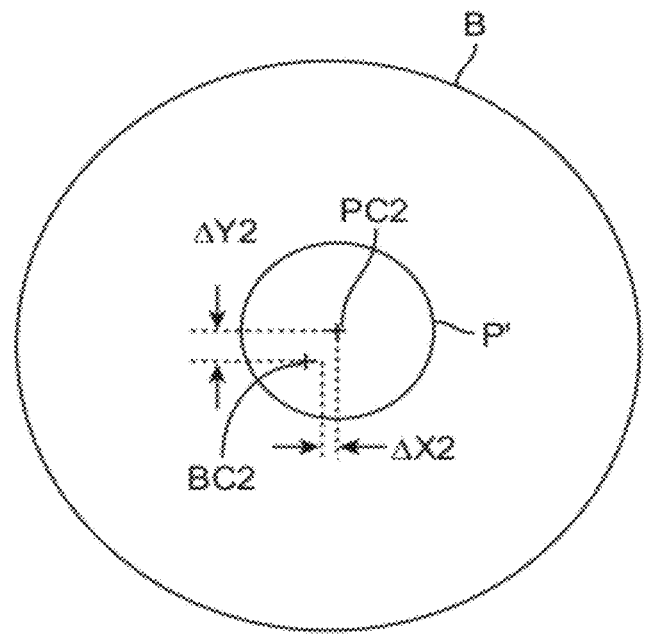
Figure 7:
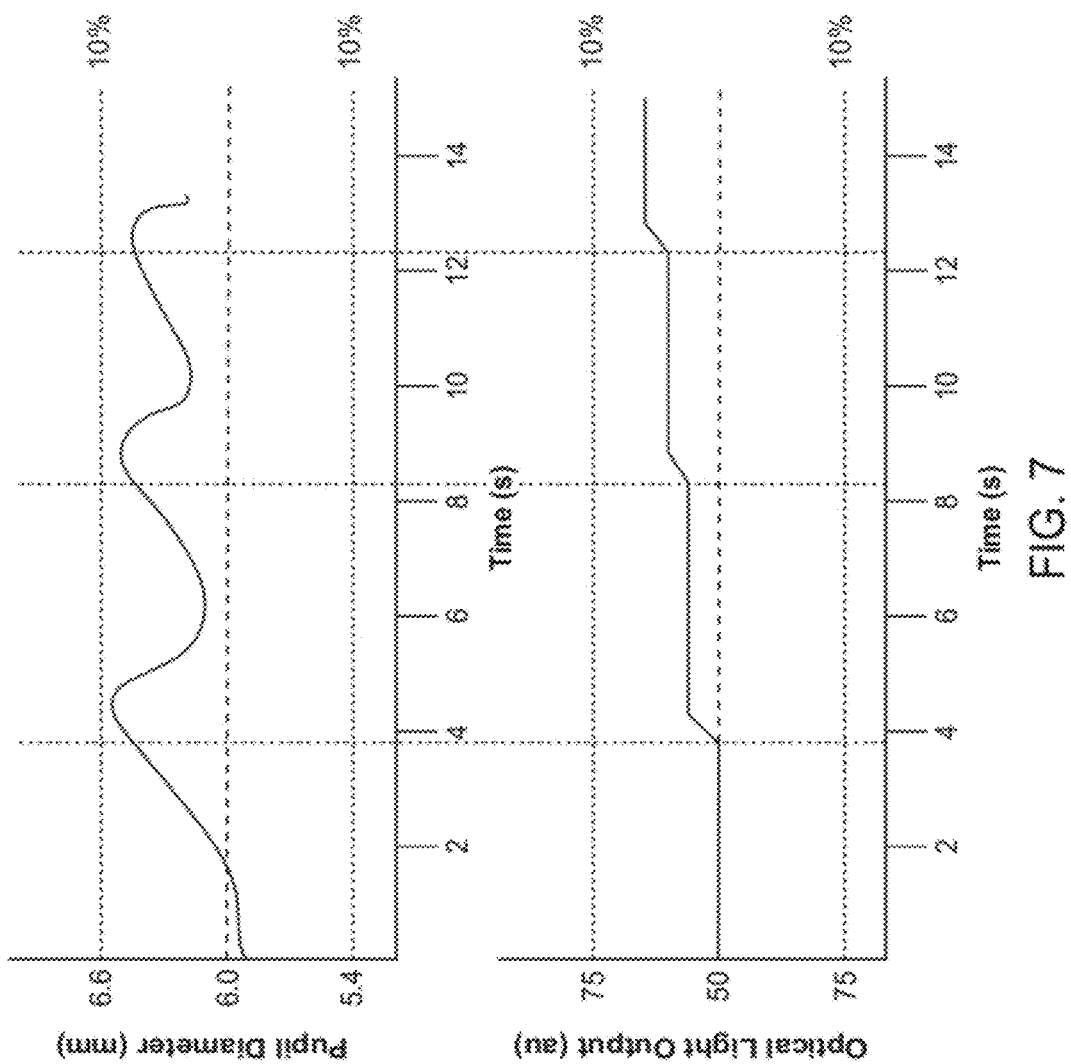
FIG. 7 graphically illustrates the operation of an embodiment of the system.

FIG. 7 show a graphic representation of the operation of an embodiment of the present invention. In one embodiment, system 10 may mitigate changes in the size of the pupil P to within certain pre-determined limits, as determined by system parameters or by input from a physician. For instance, the system may be programmed to mitigate changes in pupil size if the changes in pupil size are in excess of 10% of the target pupil size. Alternatively, the system may be programmed so that the system induces a response before the size of the pupil reaches the specified limit such that the size of the pupil stays within +/−10% of the original pupil size. As shown in FIG. 4, for example, as the change in pupil size approaches 10% of the target pupil size of 6.0 mm, system 10 increases the optical light output inducing a pupillary response and preventing the pupil dilation from exceeding the 10% limit. Similar to a thermostat operation, where the temperature is kept between the upper and lower limits, this approach keeps the pupil size within plus or minus 10% of its original diameter.

In another aspect, system 10 may impose a set of limits on the change in optical light output 32 by the variable illumination source 30 to ensure illumination levels remain at acceptable levels during the procedure. In some embodiments, a physician may be able to input a range or limits of acceptable levels of optical output. For instance, these limits could be set to plus or minus 50% relative to the original illumination output of the illumination source.

In some embodiments, the system may comprise an illumination source 30 having a variable optical light output 32 and a processor 20 for directing a desired optical light output to the eye E as a function of a pre-determined relationship or trend of pupil size change for a particular procedure. In this embodiment, a pupilometer will not be necessary to determine changes in pupil size since the optical light output will be determined as a function of the relationship. An example of one such relationship would be the standard slope of the average increase in pupil size over the duration of a procedure. For instance, if the pupil size of the average patient increases steadily by about 25% during a 10-minute LASIK procedure, the standard slope would be a 25% increase in pupil size/10-minutes. Presumably, the relationship may differ for different types of procedures or for procedures having a longer or shorter duration. In an alternate embodiment, a physician may be able to determine the relationship for an individual based on a characterization of the patient's pupil response to a range of optical light outputs. This characterization may be performed separately from the laser eye treatment procedure, such as during a routine eye exam or during wavefront mapping.

Figure 8:
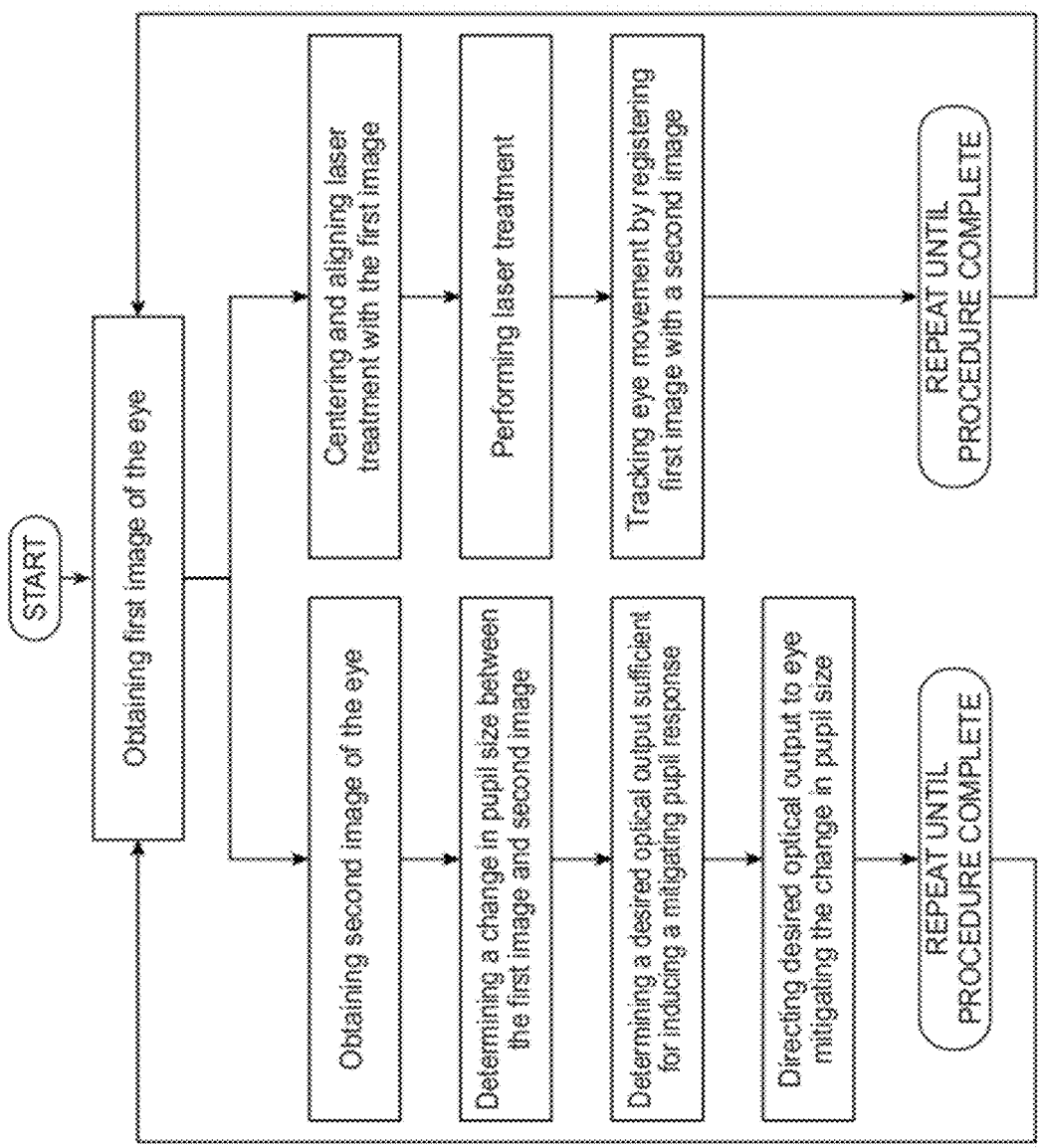
FIGS. 8-13 schematically illustrate methods of the present invention.
Figure 9:
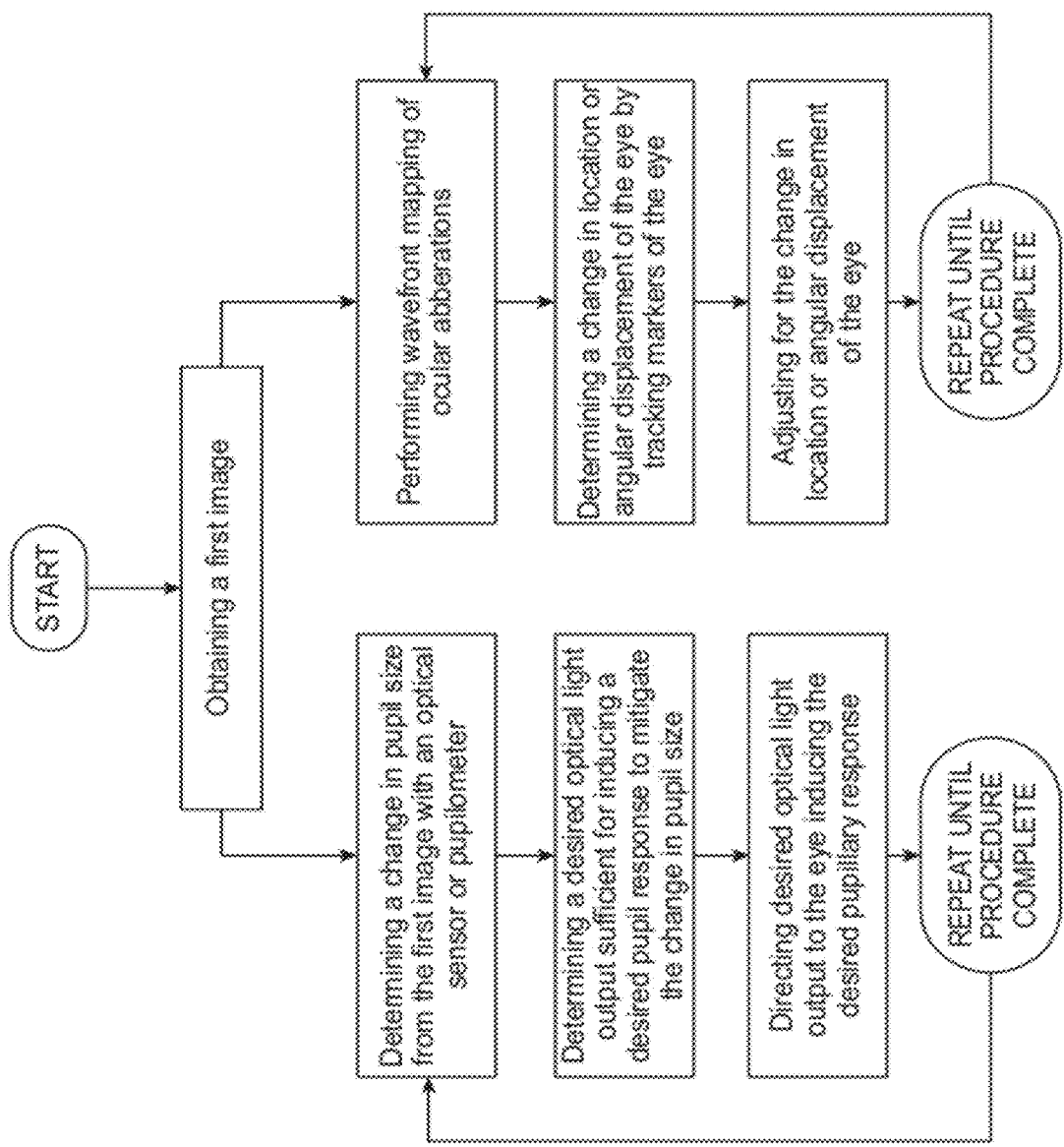
Figure 10:
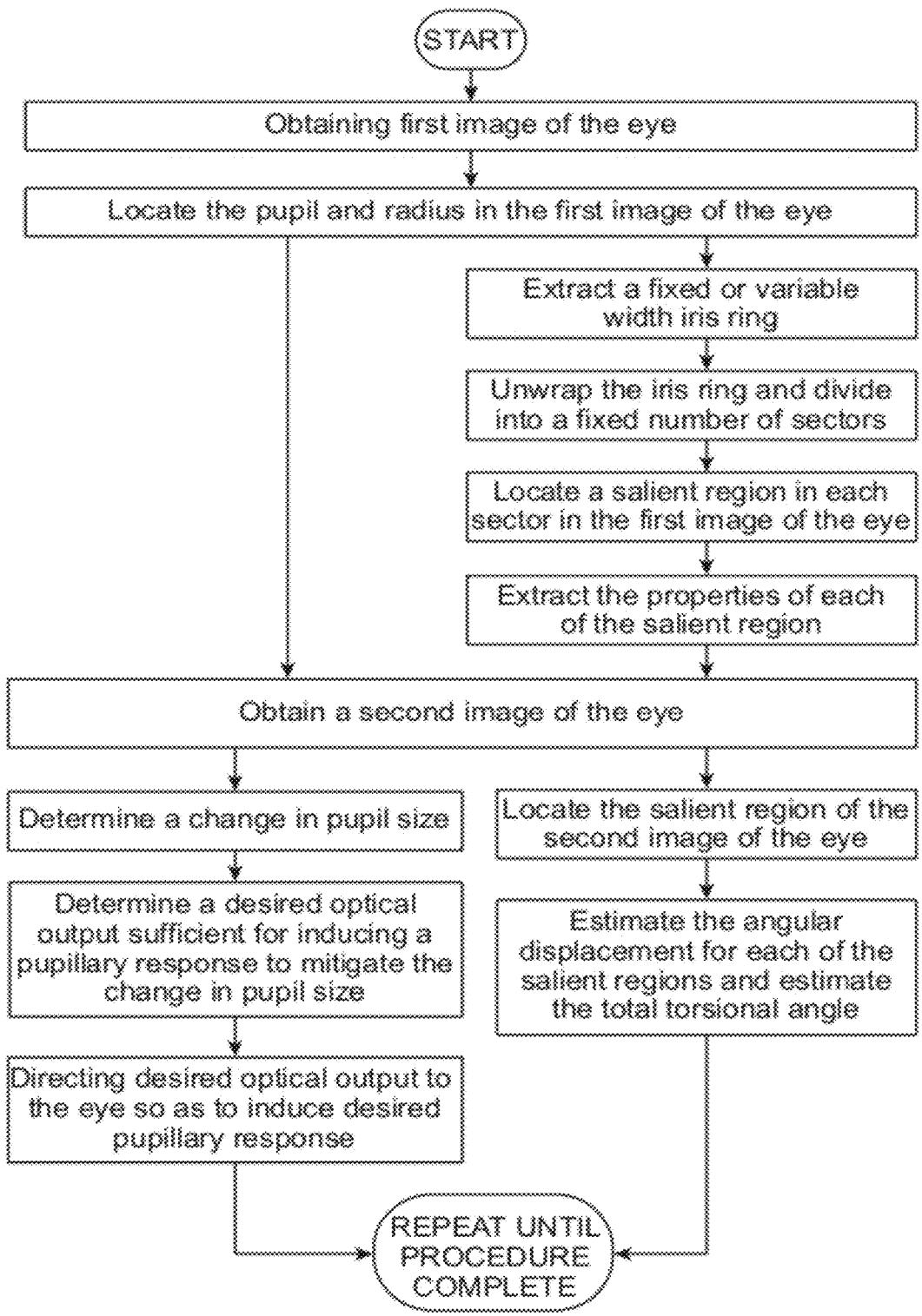

FIGS. 8-13, schematically illustrate exemplary methods of the present invention. In the example shown in FIG. 8, the method of the present invention comprises a laser eye surgery system. The method first obtains an image of the eye, centers and aligns a laser treatment with the first image, performs the laser treatment, then takes subsequent images. By determining changes in pupil size from the second image or subsequent images and the first system, determining a desired optical output sufficient to induce a pupillary response, the system mitigates change in pupil size, while contemporaneously tracking eye movement by registering the first image and subsequent images and centering and aligning subsequent laser treatments. In some embodiments, determining a pupil size change includes obtaining a first image of the eye, obtaining a second image of the eye and determining a change in pupil size between the first and second image, as shown in FIG. 8 for example. In another aspect of the invention, the method may comprise performing a diagnostic procedure, such as performing wavefront mapping of ocular aberrations, while mitigating changes in pupil size according to the present invention, as shown in FIG. 9. The method may comprise torsional tracking eye movements locating and tracking a salient region of the eye from a first image, while contemporaneously mitigating changes in pupil size according to the present invention, as shown in FIG. 10.

Figure 11:
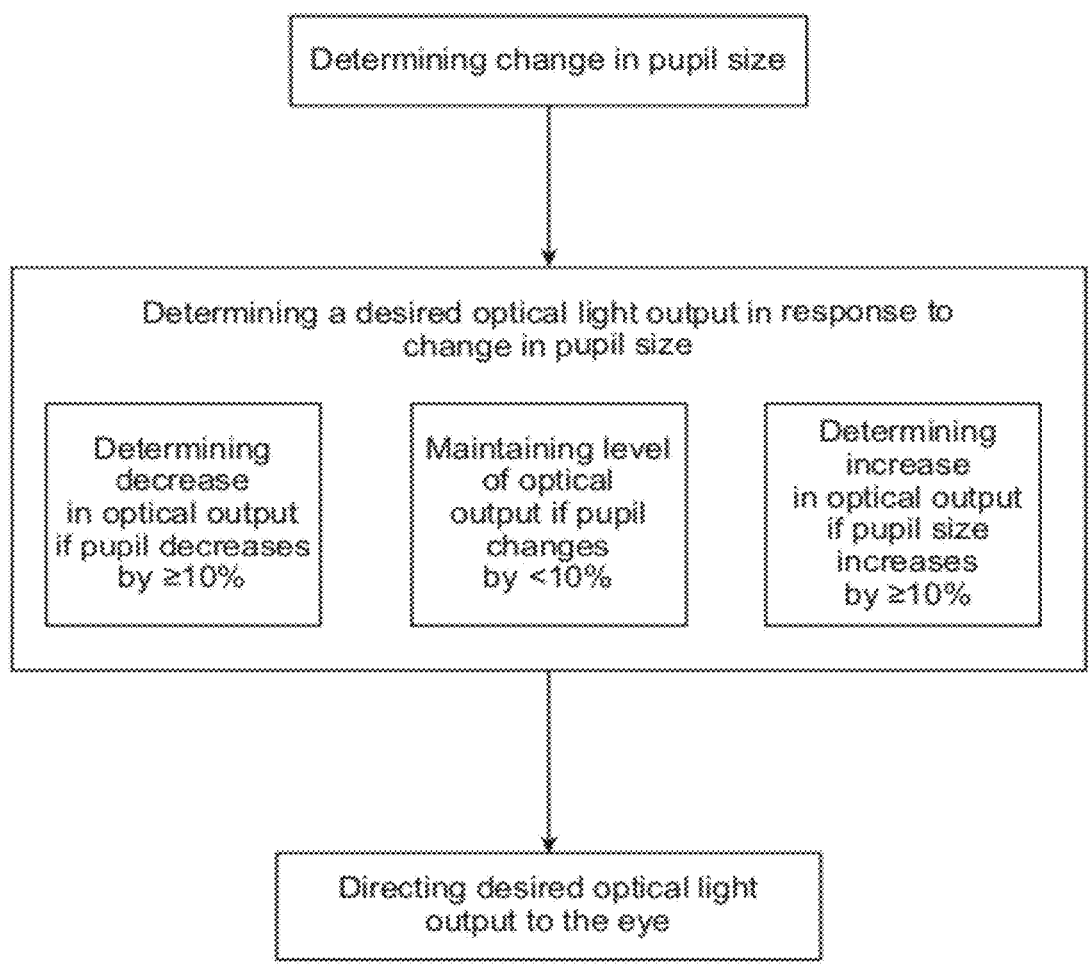
Figure 12:
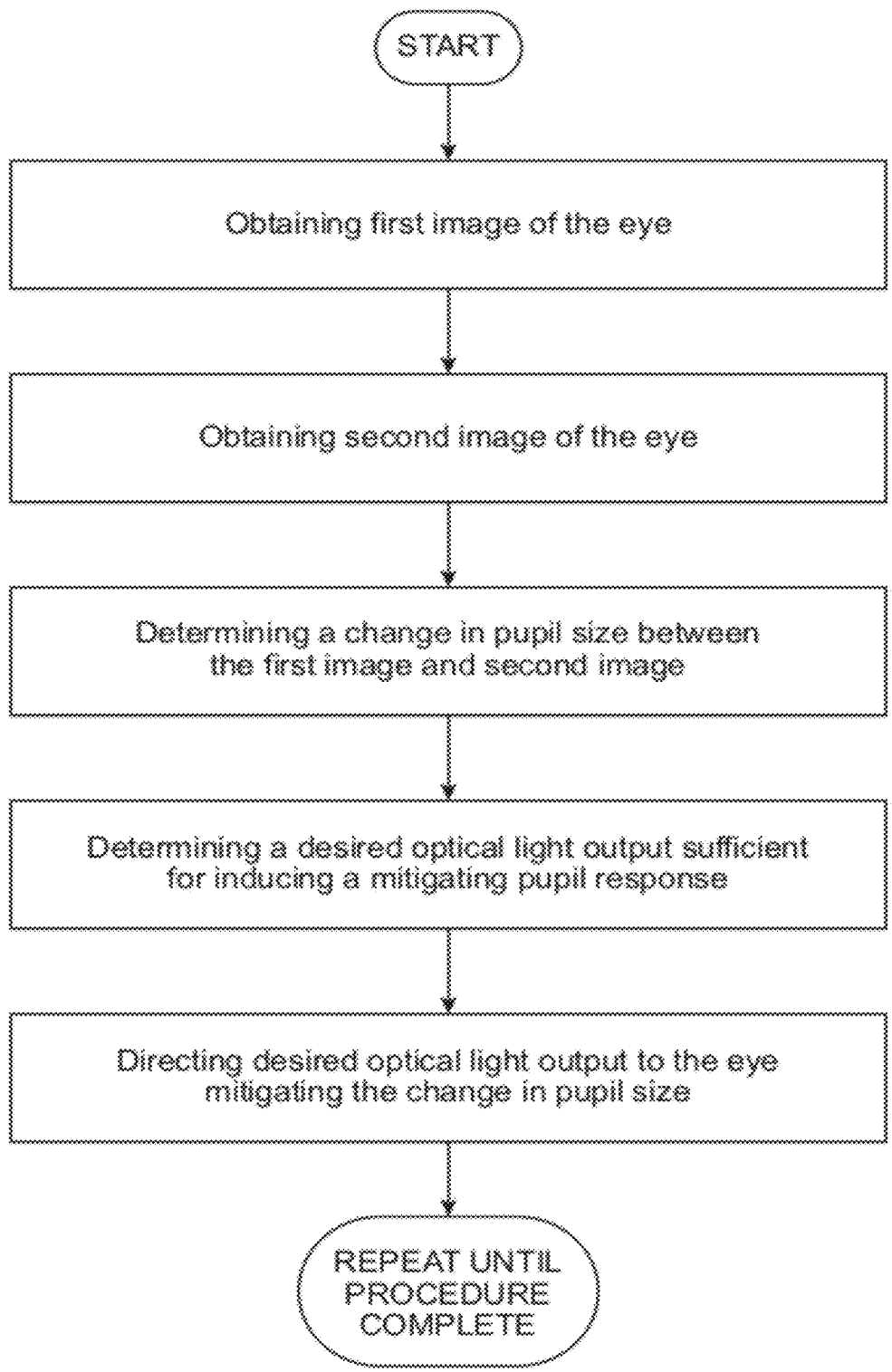
Figure 13:
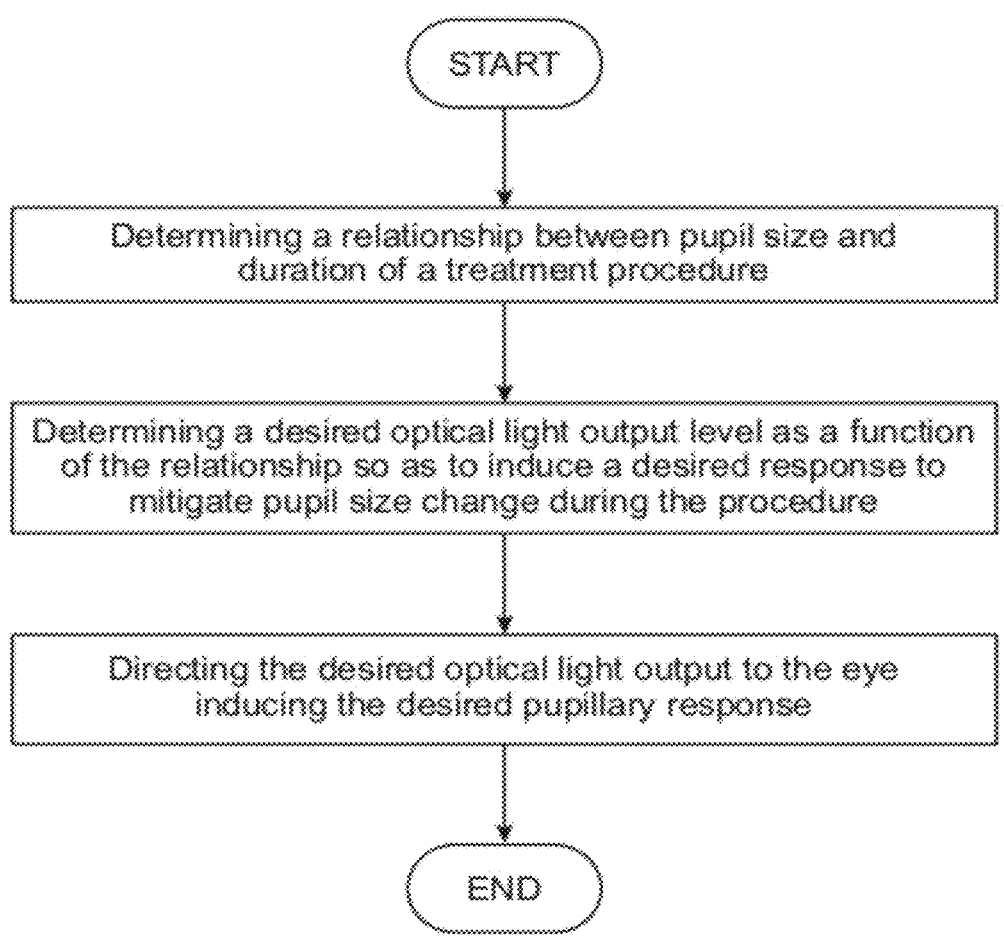

In another aspect of the invention, the method of determining optical light output in mitigating changes in pupil size may differ depending on the magnitude of the change in pupil size, for example the method may include a threshold or tolerance in which the optical light output does not change, such as <10% for example. As shown in FIG. 11, the step of determining a desired optical light in an embodiment having a pupil size change tolerance of ±10% comprises determining a decrease in optical light output if pupil size decreases by 10% or more, determining an increase in optical light output if pupil size increases by 10% or more, and maintaining the optical output level if the pupil size changes by less than 10%. FIGS. 12-13 illustrate additional embodiments of the present invention.

In some embodiments, the method includes a laser eye surgical treatment method. In these embodiments, the methods may comprise obtaining a first image of the eye and determining and mitigating subsequent changes in pupil size, while concurrently tracking eye movement and aligning the laser treatment with the eye. In other embodiments, the methods include a diagnostic procedure, such as wavefront mapping of ocular aberrations. Additionally, the present invention may be comprise a system that performs diagnostic and treatment methods.

In another embodiment, the method comprises determining a relationship of pupil size change for a given procedure, determining a desired optical output to induce a desired pupillary response to mitigate an anticipated change in pupil size as determined by a function of that relationship, and directing the desired optical output to the eye. In these embodiments, there may be no need for a pupilometer as the change in pupil size is mitigated in response to an anticipated pupil change as determined by a function or anticipate rate of pupil change. For instance, if the eye of the average patient increases at a rate of 0.2 mm/second for a given procedure, the anticipate rate of pupil change during the procedure would be 0.2 mm/second. A method utilizing a function of anticipate pupil change may comprise automatically increasing the optical light output sufficient to induce a response in the average eye that would mitigate the anticipated change in pupil size according to the average rate. Additionally, the anticipated rate may take into account the patient's age, eye characteristics, or be customized for a given patient.

While the exemplary embodiments have been described in some detail for clarity of understanding and by way of example, a variety of adaptations, modifications, and changes will be obvious to those of skill in the art. For example, the processor may employ dynamic thresholding in measurements of the pupil and outer iris boundary. Additionally, any of the features or elements of the described embodiments may be combined or interchanged so as to customize the system and/or method to mitigate changes in pupil size as needed for a given procedure.

What is claimed is:

1. A method for mitigating a change in pupil size of an eye of a patient while an ophthalmological procedure is performed on the eye of the patient, the method comprising:
    obtaining a first image of the eye with an imaging device at a first lighting condition at the eye;
    obtaining a second image of the eye with the imaging device at the first lighting condition at the eye;
    determining the change in pupil size by using the first and second images;
    determining, with a processor, a desired optical light output corresponding to a second lighting condition at the eye different from the first lighting condition, in response to the change in pupil size, the desired optical light output configured to induce a desired pupillary response mitigating the change in pupil size; and
    directing the desired optical light output from a variable illumination source to the eye while the ophthalmological procedure is performed on the eye of the patient, thereby providing the second lighting condition at the eye that mitigates the change in pupil size during performance of the ophthalmological procedure,
    wherein the ophthalmological procedure comprises a wavefront measurement of the eye, a laser ablation treatment of the eye, or a wavefront measurement and a laser ablation treatment of the eye.

2. The method of claim 1, wherein determining the change in pupil size comprises registering the first and second images.

3. The method of claim 1, wherein the ophthalmological procedure comprises the laser ablation treatment, and wherein the laser ablation treatment comprises centering and aligning an ablation profile with the first image of the eye.

4. The method of claim 3, wherein centering and aligning further comprises centering and torsionally aligning the ablation profile with the first image of the eye.

5. The method of claim 3, further comprising tracking a reference point of the eye from a first image to a second image of the eye;
    registering the first and second image of the eye by matching a common reference point in the first and second images; and
    centering and aligning the ablation profile with the second image of the eye.

6. The method of claim 5, wherein the reference point comprises a member selected from the group consisting of an iris feature and a pupil center location.

7. The method of claim 1, wherein the change in pupil size comprises a change in pupil size that exceeds a pre-determined tolerance of the pupil size in the first image.

8. The method of claim 7, wherein the pupil size tolerance is approximately ±10% of the first pupil size.

9. The method of claim 1, wherein determining the desired optical light output comprises determining an optical light output within a pre-determined range of optical light outputs.

10. The method of claim 9, wherein the pre-determined range is sufficient for performing a procedure on the eye.

11. The method of claim 10, wherein the pre-determined range is within a certain optical output tolerance of a reference optical output.

12. The method of claim 11, wherein the certain optical output tolerance is ±50% of the reference optical output.

13. The method of claim 1, wherein determining the desired optical light output in response to the change in pupil size further comprises:
    determining an increase in optical light output to induce pupil constriction in response to an increase in pupil size so as to mitigate the increase in pupil size.

14. The method of claim 13, wherein determining the desired optical light output in response to the change in pupil size further comprises:
    determining a decrease in optical light output to induce pupil dilation in response to a decrease in pupil size so as to mitigate the decrease in pupil size.

15. The method of claim 14, wherein the induced dilation corresponds roughly to the measured decrease in pupil size, and wherein the induced constriction corresponds roughly to the measured increase in pupil size, so as to induce a pupillary response with the directed desired optical output so as to mitigate the change in pupil size.

16. The method of claim 15, wherein the induced pupil dilation or constriction substantially maintains the size of the pupil to substantially the size of the pupil in the first image so as to mitigate changes in pupil size during at least a portion of a diagnostic or treatment procedure.

17. The method of claim 16, wherein the induced pupil dilation or constriction maintains the size of the pupil to a size within ±10% of the size of the pupil in the first image.

18. A method for performing an ophthalmological procedure on an eye of a patient, the eye having a pupil, the method comprising:
determining a trend in pupil size change during performance of the ophthalmological procedure at a first lighting condition at the eye;
determining, with a processor, a desired light output corresponding to a second lighting condition at the eye different from the first lighting condition in response to the trend in pupil size change at the first lighting condition, such that the desired light output induces a desired pupillary response to mitigate the trend in pupil size change during performance of the ophthalmological procedure; and
directing the desired light output from a variable illumination source to the eye while the ophthalmological procedure is performed on the eye of the patient thereby providing the second lighting condition at the eye that mitigates the trend in pupil size change during performance of the ophthalmological procedure,
wherein the ophthalmological procedure comprises a wavefront measurement of the eye, a laser ablation treatment of the eye, or a wavefront measurement and a laser ablation treatment of the eye.

19. The method of claim 18, wherein the trend is based on a member selected from the group consisting of an average pupil change response during a procedure, a median pupil change response during a procedure, and a mode of pupil change response during a procedure.

20. The method of claim 18, wherein the trend of pupil size changes is based in part on patient and/or procedure variables.

21. The method of claim 20, wherein patient variables include any of age, gender, physiological indicators, and refractive characteristics of the eye.

22. The method of claim 20 wherein procedure variables include any of length of treatment, depths of ablations, intensity of laser, and type of procedure.

23. A method for performing an ophthalmological procedure on an eye, the eye having a pupil, the method comprising:
determining a change in pupil size with an optical sensor at a first substantially constant lighting condition;
determining, with a processor, a desired optical light output corresponding to a second lighting condition different from the first lighting condition in response to the change in pupil size at the first lighting condition, such that the desired light output induces a desired pupillary response mitigating the change in pupil size; and
directing the desired optical light output from a variable illumination source to the eye while the ophthalmological procedure is performed on the eye of the patient thereby providing the second lighting condition at the eye that mitigates the change in pupil size during performance of the ophthalmological procedure,
wherein the ophthalmological procedure comprises a wavefront measurement of the eye, a laser ablation treatment of the eye, or a wavefront measurement and a laser ablation treatment of the eye.

24. A method for performing an ophthalmological procedure on an eye refractive errors of a patient, the eye having a pupil, the method comprising:
directing a desired optical light output from a variable illumination source to the eye corresponding to a second lighting condition at the eye thereby mitigating a change in pupil size by varying the optical light output according to a function, wherein the function is based on a relationship between:
a change in pupil size at a first lighting condition, wherein the first lighting condition is substantially constant and different from the second lighting condition; and
a duration of the ophthalmological procedure; and
performing the ophthalmological procedure concurrent with directing the desired optical light output,
wherein the ophthalmological procedure comprises a wavefront measurement of the eye, a laser ablation treatment of the eye, or a wavefront measurement and a laser ablation treatment of the eye.

25. The system of claim 24, wherein the relationship comprises a standard slope of change in pupil size over time during the ophthalmological procedure.

26. The system of claim 25, wherein the ophthalmological procedure is the laser ablation treatment of the eye.

27. A system for performing an ophthalmological procedure on an eye of a patient, the eye having a pupil, the system comprising:
a pupilometer generating a pupil size signal;
an illumination source having a variable optical light output; and
a processor coupled with the pupilometer and the illumination source, the processor configured to transmit an optical light output command signal to the illumination source in response to a detected change in pupil size at a first substantially constant lighting condition based on the pupil size signal, wherein the optical light output command signal corresponds to a change in lighting condition from the first lighting condition to a second lighting condition different from the first lighting condition, so as to mitigate a change in pupil size during performance of the ophthalmological procedure,
wherein the ophthalmological procedure comprises a wavefront measurement of the eye, a laser ablation treatment of the eye, or a wavefront measurement and a laser ablation treatment of the eye.

28. The system of claim 27, wherein the pupilometer and the illumination source are in optical communication with the eye, and wherein the processor comprises tangible media embodying machine-readable code for determining the optical light output command signal in response to the pupil size signal.

29. The system of claim 28, wherein the processor is coupled with the pupilometer such that pupil size signal from the pupilometer is receivable by the processor.

30. The system of claim 29, wherein the pupilometer comprises an optical sensor and a processor.

31. The system of claim 29, wherein the processor of the pupilometer and the processor of the system are the same processor.

32. The system of claim 30, wherein the pupilometer comprises an imaging device and a processor.

33. The system of claim 29, wherein the processor is coupled with the illumination source such that the processor controls the optical light output of the illumination source.

34. The system of claim 33, wherein the processor comprises a dynamic feedback mechanism configured to direct optical light output in response to changes in pupil size as determined by the processor from the received pupil size signals.

35. The system of claim 27, wherein the processor is configured to control optical light output based on a relationship between: changes in pupil size; and optical light output.

36. The system of claim 27, wherein the illumination source comprises an illumination source having differing levels of brightness.

37. The system of claim 27, wherein the illumination source comprises a member selected from the group consisting of an ambient light, a halogen ring, an illuminated viewing target, and an LED.

38. The system of claim 27, wherein the illumination source comprises one or more illumination sources.

39. The system of claim 27, wherein the illumination source comprises one or more static illumination sources.

40. The system of claim 28, wherein the tangible media comprises electronic recordings of a plurality of pupil sizes and associated brightness levels.

41. The system of claim 27, further comprising a tracking system configured to track a feature of the eye during a laser eye surgical procedure.

42. The system of claim 41, wherein the tracking system is configured to track cyclotorsional movement of the eye during a laser eye surgical procedure.

43. A system for performing an ophthalmological procedure on an eye of a patient, the eye having a pupil, the system comprising:

an illumination source having a variable optical light output; and a processor coupled with the illumination source, the processor configured to transmit an optical light output command signal to the illumination source so as to produce a desired lighting condition at the eye according to a function of pupil size change over time during performance of the ophthalmological procedure on the eye, wherein the function is based on a relationship between:

a change in pupil size at a first substantially constant lighting condition; and a duration of the performance of the ophthalmological procedure on the eye, wherein the ophthalmological procedure comprises a wavefront measurement of the eye, a laser ablation treatment of the eye, or a wavefront measurement and a laser ablation treatment of the eye.

44. The system of claim 43, wherein the relationship comprises a standard slope of pupil size over time during the performance of the ophthalmological procedure on the eye.

45. The method of claim 1, wherein the ophthalmological procedure comprises the wavefront measurement of the eye.

46. The method of claim 1, wherein the ophthalmological procedure comprises the laser ablation treatment of the eye.

* * * * *